United States Patent
Waterson et al.

[11] Patent Number: 6,090,813
[45] Date of Patent: Jul. 18, 2000

[54] USE OF OXIDO-SQUALENE CYCLASE INHIBITORS TO LOWER BLOOD CHOLESTEROL

[75] Inventors: David Waterson; Elaine Sophie Elizabeth Stokes; George Robert Brown; Robin Wood, all of Macclesfield, United Kingdom

[73] Assignee: Zeneca Limited, London, United Kingdom

[21] Appl. No.: 09/011,718

[22] PCT Filed: Aug. 14, 1996

[86] PCT No.: PCT/GB96/01985

§ 371 Date: Feb. 13, 1998

§ 102(e) Date: Feb. 13, 1998

[87] PCT Pub. No.: WO97/06802

PCT Pub. Date: Feb. 27, 1997

[30] Foreign Application Priority Data

Aug. 15, 1995 [GB] United Kingdom ............... 9516709

[51] Int. Cl.[7] ............................................. A01N 43/60
[52] U.S. Cl. ........................... 514/255; 514/252; 514/218; 540/492; 540/575; 544/358; 544/360
[58] Field of Search ........................ 514/252, 218, 514/255; 540/492, 575; 544/358, 360

[56] References Cited

U.S. PATENT DOCUMENTS

| | | | |
|---|---|---|---|
| 4,167,567 | 9/1979 | McCall | 424/250 |
| 5,371,091 | 12/1994 | Mistra | 514/314 |
| 5,411,971 | 5/1995 | Edmonds-Alt et al. | 514/318 |
| 5,606,065 | 2/1997 | Emonds-Alt et al. | 546/223 |
| 5,856,326 | 5/1999 | Anthony et al. | 514/252 |

FOREIGN PATENT DOCUMENTS

| | | |
|---|---|---|
| 1 449 100 | 9/1976 | United Kingdom . |
| WO 92/18478 | 10/1992 | WIPO . |
| 96/10022 | 4/1996 | WIPO . |
| WO 96/26196 | 8/1996 | WIPO . |
| WO 9/30343 | 10/1996 | WIPO . |

OTHER PUBLICATIONS

Tabacik et al: "Squalene expoxidase, oxido–squalene cyclase and cholesterol biosynthesis in normal and tumoral mucosa of the human gastrointestinal tract. Evidence of post–HMGCoA regulation.", Biochem. Biophys. ACTA, vol. 666, no. 3, 1982 pp. 433–441, XP000610864.

Cattel et al:"Drug design based on biosynthetic studies: synthesis, biological activity, and kinetics of new inhibitors of 2,3–oxidosualene cyclase and squalene epoxidase.", Steriods., vol. 53, no 3–5, 1989, pp. 363–391, XP000611661.

Satori et al., Synthesis and analgesic activities of urea derivatives of β–amino–N–pyridyl benzene propanamide.

*Primary Examiner*—Mukund J. Shah
*Assistant Examiner*—Pavanaram K Sripada
*Attorney, Agent, or Firm*—Pillsbury Madison & Sutro, LLP

[57] ABSTRACT

A compound of formula (I), or a pharmaceutically acceptable salt thereof, wherein G, $T^1$, $T^2$ and $T^3$ are selected from CH and N; provided that $T^2$ and $T^3$ are not both CH; A is selected from a direct bond and (1–4C)alkylene; X is selected from oxy, thio, sulphinyl, sulphonyl, carbonyl, carbonylamino, N-di-(1–6C)alkylcarbonylamino, sulphonamido, methylene, (1–4C)alkylmethylene and di-(1–6C)alkylmethylene, and when $T^2$ is CH, X may also be selected from aminosulphonyl and oxycarbonyl; and Q is selected from (5–7C)cycloalkyl, a heterocyclic moiety containing up to 4 heteroatoms selected from nitrogen, oxygen and sulphur, phenyl, naphthyl, phenyl(1–4C)alkyl and phenyl(2–6C)alkenyl; for the manufacture of a medicament for treating diseases or medical conditions in which an inhibition of oxido-squalene cyclase is desirable.

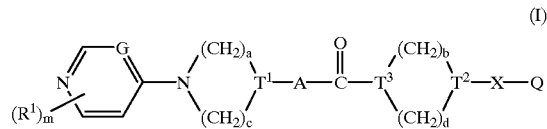

(I)

16 Claims, No Drawings

USE OF OXIDO-SQUALENE CYCLASE INHIBITORS TO LOWER BLOOD CHOLESTEROL

This invention concerns heterocyclic derivatives which are useful in inhibiting oxido-squalene cyclase, processes for their preparation and pharmaceutical compositions containing them. The present invention is also concerned with heterocyclic derivatives capable of inhibiting cholesterol biosynthesis and hence in lowering cholesterol levels in blood plasma. The present invention also relates to methods of using such heterocyclic derivatives in diseases and medical conditions such as hypercholesterolemia and atherosclerosis.

There is evidence that high serum cholesterol levels are an important risk factor in coronary heart disease and associated diseases such as atherosclerosis and ischaemic heart disease. As a result there has been a great deal of interest in finding ways of lowering cholesterol levels in blood plasma. Althought it has been possible to obtain some reduction my means of diet, only modest reductions have been obtained by controlling the dietry intake of cholesterol. Consequently, there is a need for therapeutic approaches to reducing cholesterol levels.

Several different classes of compounds have been reported to possess the capability of being able to lower cholesterol levels in blood plasma. For example agents which inhibit the enzyme HMGCoA reductase, which is essential for the production of cholesterol, have been reported to reduce levels of serum cholesterol. Illustrative of this class of compounds in the HMGCoA reductase inhibitor known as lovastatin which is disclosed in U.S. Pat. No 4,231,938. Other agents which are reported to lower serum cholesterol include those which art by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promotes replacement of bile acids by synthesis in the liver from cholesterol, which results in an upregultion of the hepatic LDL cholesterol receptor and in alowering of circulating blood cholesterol levels.

The biosynthesis of cholesterol is a complex process which will be considered here as three principal stages, namely 1) the conversion of acetic acid to mevalonic acid 2) the conversion of mevalonic acid to squalene and 3) the conversion of squalene to cholesterol. In the last stage, squalene is first converted into 2,3-oxido-squalene and then to lanosterol. Lanosterol is then converted to cholesterol through a number of enzymnatic steps.

The conversion of 2,3-oxido-squalene to lanosterol is a key step in the biosynthesis of cholesterol. This conversion is catalysed by the enzyme oxido-squalene cyclase. It follows that inhibition of this enzyme decreases the amount of lanosterol available for conversion to cholesterol. Consequently, inhibition of oxido-squalene cyclase should interupt cholesterol biosynthesis and give rise to a lowering of cholesterol levels in blood plasma via LDL receptor upregulation.

The present invention is based on the discovery that certain heterocyclic derivatives are inhibitors of oxido-squalene cyclase and are hence useful in treating diseases and medical conditions in which inhibition of oxido-squalene cyclase is desirable.

According to the present invention there is provided the use of a compound of formula I (set out hereinafter together with the other formulae referred to herein), or a pharmaceutically acceptable salt thereof, wherein:

G is selected from CH and N;

$T^1$ is selected from CH and N;

$R^1$ is hydrogen, amino, halogeno, cyano, (1–6C)alkyl or (1–6C)alkoxy;

m is 1 or 2;

A is selected from a direct bond and (1–4C)alkylene;

$T^2$ is selected from CH and N;

$T^3$ is selected from CH and N; provided that $T^2$ and $T^3$ are not both CH;

a and b are independently selected from 2 and 3;

c and d are independently selected from 1 and 2;

wherein the heterocyclic ring containing $T^1$ and the heterocyclic ring containing $T^2$ may, independently, be optionally substituted by one or more substituents selected from (1–6C)alkyl, (1–6C)alkoxy, phenyl(1–4C)alkyl, halogeno and (1–6C)alkoxycarbonyl;

X is selected from oxy, thio, sulphinyl, sulphonyl, carbonyl, carbonylamino, N-di-(1–6C)alkylcarbonylamino, sulphonamido, methylene, (1–4C)alkymethylene and di-(1– 6C)alkylmethylene, and when $T^2$ is CH, X may also be selected from aminosulphonyl and oxycarbonyl;

Q is selected from (5–7C)cycloalkyl, a heterocyclic moiety containing up to 4 heteroatoms selected from nitrogen, oxygen and sulphur; phenyl, naphthyl, phenyl (1–4C)alkyl and phenyl(2–6C)alkenyl, and wherein the last three groups may optionally bear a phenyl substituent;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno (1–6C)alkyl, (1–6C)alkanoyl, tetrazolyl and a heteroaryl group comprising a 5- or 6-membered monocyclic ring conatining up to three heteroatoms selected from nitrogen, oxygen and sulphur; for the manufacture of a medicament for treating diseases or medical conditions in which an inhibition of oxido-squalene cyclase is desirable.

The chemical formulae referred to herein by Roman numerals are, for convenience, set out on a separate sheets following the Examples.

The compounds of the present invention are oxido-squalene cyclase inhibitors and hence possess the property of inhibiting cholesterol biosynthesis. Accordingly, there is also provided the use of a compound of formula I, or a pharmaceutically acceptable salt thereof, for the manufacture of a medicament for inhibiting cholesterol biosynthesis. Thus the compounds of the present invention will be useful in treating diseases or medical conditions in which an inhibition of oxido-squalene cyclase is desirable, for example those in which a lowering of the level of cholesterol in blood plasma is desirable. In particular, the compounds of the present invention will be useful in treating hypercholesterolemia and/or ischaemic diseases associated with atheromatous vascular degeneration such as atherosclerosis. As inhibitors of cholesterol biosynthesis, the compounds of the present invention will also be useful in treating fungal infections.

Thus according to a further feature of the present invention there is provided a method of inhibiting oxido-squalene cyclase in a warm-blooded animal (such as man) requiring such treatment, which method comprises adminstering to said animal an effective amount of a compound of formula I, or a pharmaceutically-acceptable salt thereof. In particular, the present invention provides a method of inhibiting cholesterol biosynthesis, and more particularly to a method of treating hypercholesterolemia and atheromatous vascular degneration (such as atherosclerosis).

Thus the present invention also provides the use of a compound of formula I, or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

In particular, the compounds of the present invention are potentially useful in inhibiting cholesterol biosynthesis in man and hence in treating the above-mentioned medical conditions in man.

The present invention also provides a compound of formula I, or a pharmaceutically-acceptable salt thereof wherein G, $T^1$, A, $T^2$, X and Q are as defined above.

It will be understood that when formula I compounds contain a chiral centre, the compounds of the invention may exist in, and be isolated in, optically active or racemic form. The invention includes any optically active or racemic form of a compound of formula I which possesses the beneficial pharmacological effect of inhibiting oxido-squalene cyclase. The synthesis of optically active forms may be carried out by standard techniques of organic chemistry well known in the art, for example by, resolution of a racemic form, by synthesis from optically active starting materials or by asymmetric synthesis. It will be appreciated that certain compounds of formula I may exist as geometrical isomers. The invention includes any geometrical isomer of a compound of formula I which possesses the beneficial pharmacological effect of inhibiting oxido-squalene cyclase.

It will also be understood that certain compounds of the present invention may exist in solvated, for example hydrated, as well as unsolvated forms. It is to be understood that the present invention encompasses all such solvated forms which possess the property of inhibiting oxido-squalene cyclase.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

Particular values for optional substituents which may be present on Q include, for example,

| | |
|---|---|
| for alkyl; | (1–4C)alkyl, such as methyl, ethyl, propyl, isopropyl, butyl, isobutyl, sec-butyl or tert-butyl; |
| for cycloalkyl | cyclopropyl, cyclobutyl or cyclopenty; |
| for cycloalkylalkyl | (3–6C)cycloalkyl(1–2C)alkyl such as cyclopropylmethyl, cyclopropylethyl, cyclobutylmethyl or cyclopentylmethyl; |
| for alkenyl; | (2–4C)alkenyl, such as allyl, prop-1-enyl, 2-methyl-2-propenyl or 2-butenyl; |
| for alkynyl; | (2–4C)alkynyl, such as prop-2-ynyl or but-2-ynyl; |
| for alkoxy; | (1–6C)alkoxy, such as methoxy, ethoxy, propoxy, isopropoxy, butoxy, pentoxy or 3-methylbutoxy; |
| for alkylamino; | (1–4C)alkylamino, such as methylamino, ethylamino, propylamino or butylamino; |
| for di-alkylamino; | di-[(1–4C)alkyl]amino such as dimethylamino, diethylamino, methylpropylamino or dipropylamino; |
| for alkylcarbamoyl; | (1–4C)alkylcarbamoyl such as N-methylcarbarnoyl, N-ethylcarbamoyl, N-propylcarbamoyl, N-butylcarbamoyl or N-tert-butylcarbamoyl or (N-(2-methylpropyl)carbamoyl; |
| for di-alkylcarbamoyl; | di-[(1–4C)alkyl]carbamoyl, N,N-dimethylcarbamoyl or N,N-diethylcarbamoyl; for |
| alkoxycarbonyl; | (1–4C)alkoxycarbamoyl such as methoxycarbonyl, ethoxycarbonyl, propoxycarbonyl, iso-propoxycarbonyl, butyoxycarbonyl or tert-butoxycarbonyl; |
| for alkylthio; | (1–4C)alkylthio such as methylthio, ethylthio, propylthio, isopropylthio or butylthio; |
| for alkylsulphinyl; | (1–4C)alkylsulphinyl such as methylsulphinyl, ethylsulphinyl, propylsulphinyl, isopropylsulphinyl or butylsulphinyl; |
| for alkylsulphonyl; | (1–4C)alkylsulphonyl such as methylsulphonyl, ethylsulphonyl, propylsulphonyl, isopropylsulphonyl or butylsulphonyl; |
| for halogeno; | fluoro, chloro, bromo or iodo; |
| for halogenoalkyl; | halogeno(1–4C)alkyl such as halogenoalkyl containing one, two or three halo groups selected from fluoro, chloro, bromo and iodo and an alkyl group selected from methyl, ethyl, propyl, iso-propyl, butyl, iso-butyl and sec-butyl, thus particular values will include trifluromethyl, difluoromethyl and fluoromethyl; |
| for alkanoylamino; | (1–4C)alkanoylamino such as formamido, acetamido, propionamido, isopropionamido, butyramido and iso-butyramido; |
| for alkylenedioxy; | methylenedioxy or ethylenedioxy; |
| for alkanoyl; | (1–4C)alkanoyl such as formyl, acetyl, propionyl or butyryl; |

Particular values for Q when it is a heterocyclic moiety containing up to 4 heteroatoms selected from the-group consisting of nitrogen, oxygen and sulphur are, for example, a 5- or 6-membered heterocyclic moiety which is a single ring or is fused to one or two benzo rings such as furyl, benzofuranyl, tetrahydrofuryl, chromanyl, thienyl, benzothienyl, pyridyl, piperidinyl, quinolyl, 1,2,3,4-tetrahydroquinolinyl, isoquinolyl, 1,2,3,4-tetrahydroisoquinolinyl, pyrazinyl, piperazinyl, pyrimidinyl, pyridazinyl, quinoxalinyl, quinazolinyl, cinnolinyl, pyrrolyl, pyrrolidinyl, indolyl, indolinyl, imidazolyl, benzimidazolyl, pyrazolyl, indazolyl, oxazolyl, benzoxazolyl, isoxazolyl, thiazolyl, benzothiazolyl, isothiazolyl, morpholinyl, 4H-1,4-benzoxazinyl, 4H-1,4-benzothiazinyl, 1,2,3-triazolyl, 1,2,4-triazolyl, oxadiazolyl, furazanyl, thiadiazolyl, tetrazolyl, dibenzofuranyl and dibenzothienyl, which may be attached through any available position including, for an appropriate X group such as, for example, carbonyl and methylene, through any available nitrogen atom and which may bear up to three substituents including a substituent on any available nitrogen atom.

Particular values for Q when it is heteroaryl which comprises a 5- or 6-membered monocyclic heteroaryl ring containing up to 3 heteroatoms selected from the group consisting of oxygen nitrogen and sulphur are, for example, furyl, thienyl, pyridyl, pyrazinyl, pyrimidinyl, pyridazinyl, pyrrolyl, pyrazolyl, oxazolyl, isoxazolyl, thiazolyl, isothiazolyl, 1,2,3-triazolyl, 1,2,4-triazolyl, oxadiazolyl, furazanyl and thiadiazolyl which may be attached through any available position including through any available nitrogen atom.

Particular values for Q when cycloalkyl include, for example, cyclopentyl and cyclohexyl.

Particular values for optional substituents on the heterocyclic rings containing $T^1$ and $T^2$ include, for example, lamino group it is the sulphonyl group therein which is attached to $T^2$ whereas, when X is an aminosulphonyl group, the sulphonyl group therein is attached to Q.

In general, it is preferred that X is, for example, $CH_2$, S, CO or $SO_2$.

In general, the heterocyclic rings containing $T^1$ and $T^2$ will be unsubstituted or bear one or two substituents selected from those hereinbefore defined.

In general, Q will be unsubstituted or will bear one, two or three (preferably one or two) substituents selected from those hereinbefore defined.

In general, it is preferred, for example, that A is a direct bond.

In general it is preferred, for example, that when T is N, X is selected from $CH_2$, CO and $SO_2$; when $T^2$ is CH, X is selected from S and CO.

In general it is preferred, for example, that Q is phenyl, naphthyl or phenyl(2–6C)alkenyl (such as styryl) or a heteroaryl group as herein before defined (such as thienyl).

Specific values for A include a direct bond and methylene.

Specific values for optional substituents on the heterocyclic ring containing $T^1$ or the heterocyclic ring containg $T^2/T^3$ include, for example (1–6C)alkyl (such as methyl) and (1–6C)alkoxycarbonyl (such as methoxycarbonyl or ethoxycarbonyl).

Specific values for X include, for example, $SO_2$, S, O, CO, $CH_2$ and CONH.

Specific values for optional substituents for Q include, for example, halogeno (such as fluoro, chloro, bromo or iodo), (1–6C)alkoxy (such as methoxy or ethoxy), (1–6C)alkyl (such as methyl, iso-propyl or t-butyl), halogeno(1–6C)alkyl (such as trifluoromethyl), di-[(1–4C)alkyl]amino (such as dimethylamino), nitro, cyano, (1–6C)alkyl (such as methyl, ethyl, propyl or butyl), (1–6C)alkanoylamino (such as acetylamino) and pyridyl.

| | |
|---|---|
| for alkyl; | (1–4C)alkyl such as methyl, ethyl, propyl, isopropyl, butyl, isobutyl, sec-butyl or tert-butyl; |
| for alkoxy; | (1–4C)alkoxy such as methoxy, ethoxy, propoxy, isopropoxy or butoxy; |
| for phenylalkyl; | phenyl (1–2C)alkyl such as benzyl, 2-phenylethyl or 1-phenylethyl |
| for halogeno; | fluoro, chloro, bromo or iodo |
| for alkoxycarbonyl; | methoxycarbonyl, ethoxycarbonyl, isopropoxycarbonyl or butyoxycarbonyl; |

A particular value for A when it is (1–4C)alkylene is, for example, methylene, ethylene, trimethylene or tetramethylene.

A particular value for Q when it is naphthyl is, for example, 1-naphthyl or 2-naphthyl.

A particular value for Q when it is phenylalkyl is, for example, phenyl(1–2C)alkyl, such as benzyl, 2-phenylethyl or 1-phenyethyl.

A particular value for Q when it is phenylalkenyl, for example, phenyl(2–4C)alkenyl such as styryl, cinnamyl or 3-phenylprop-2-enyl.

A particular value for X when it is a N-(1–4C)alkylcarbonylamino group is, for example, N-methylcarbonylamino or N-ethylcarbonylamino; when it is (1–4C)alkylmethylene is, for example, ethane-1,1-diyl or propane-1,1-diyl; and when it is di-(1–4C)alkylmethylene is, for example, propane-2,2-diyl. It is also to be understood that when X is a carbonyloxy, carbonylamino or N-(1–4C) alkylcarbonylamino group, it is the carbonyl group therein which is attached to $T^2$. Likewise when X is a sulphony- Specifc values for a, b, c and d include, for example, a=2, b=2, c=2 and d=2; a=2, b=3, c=2 and d=2.

Specific values for $R^1$ include, for example, hydrogen, amino, (1–6C)alkyl (such as methyl and halogeno (such as chloro).

Specific values for Q—X— include, for example, phenyl-$CH_2$—, phenyl-CO—, phenyl-$SO_2$, phenyl-S, naphthyl-$CH_2$—, napthyl-CO—, naphthyl-$SO_2$—, naphthyl-S— and styryl-$SO_2$—. Further specific values include thienyl-$SO_2$.

Values of Q—X— of particular interest include, for example, phenyl-$SO_2$—, phenyl-CH=CHSO$_2$—, naphthyl-S—, benzyl- and napthyl-$SO_2$—; wherein the phenyl or naphthyl moiety may be unsubstituted or may optionally bear one or more (preferably one or two) substituents selected from those hereinbefore defined.

In a particular embodiment, the heterocyclic rings containing $T^1$ and $T^2$ are unsubstituted.

Particular embodiments of the present invention include the folowing in which G, a, b, c, d, $R^1$, m, $T^1$, $T^2$, $T^3$, X and Q may take any of the values mentioned above unless stated otherwise:

(i) G is CH;
(ii) a, b, c and d are each 2;
(iii) G is CH or N, $T^1$ is CH, $T^2$ and $T^3$ are N;
(iv) G is CH or N, $T^1$ is CH, $T^2$ and $T^3$ are N, X is oxy, thio, sulphinyl or sulphonyl;
(v) G is CH or N, $T^1$ is CH, $T^2$ and $T^3$ are N, X is carbonyl, carbonylamino, N-di-(1–6C)alkylcarbonylamnino or sulphonamido;
(vi) G is CH or N, $T^1$ is CH, $T^2$ and $T^3$ are N, X is methylene, (1–4C)alkymethylene or di-(1–6C)alkylmethylene;
(vii) G is CH or N, $T^1$ is CH, $T^2$ and $T^3$ are N, X is $SO_2$;
(viii) G is CH or N, $T^1$ is CH, $T^2$ and $T^3$ are N, X is $SO_2$, Q is phenyl;
(viv) G is CH or N, $T^1$ is CH, $T^2$ and $T^3$ are N, X is $SO_2$, Q is heteroaryl; or
(vv) G is CH or N, $T^1$ is CH, $T^2$ and $T^3$ are N, X is $SO_2$, Q is naphthyl;

Further particular embodiments include those in which G, a, b, c, d, $R^1$, m, $T^1$, $T^2$, $T^3$, X and Q may take any of the values mentioned above unless stated otherwise:
(i) G is N;
(ii) a, b, c and d are each 2;
(iii) G is N, $T^1$ is CH, $T^2$ and $T^3$ are N;
(iv) G is N, $T^1$ is CH, $T^2$ and $T^3$ are N, X is oxy, thio, sulphinyl or sulphonyl;
(v) G is N, $T^1$ is CH, $T^2$ and $T^3$ are N, X is carbonyl, carbonylamino, N-di-(1–6C)alkylcarbonylamnino or sulphonamido;
(vi) G is N, $T^1$ is CH, $T^2$ and $T^3$ are N, X is methylene, (1–4C)alkymethylene or di-(1–6C)alkylmethylene;
(vii) G is N, T is CH, $T^2$ and $T^3$ are N, X is $SO_2$;
(viii) G is N, $T^1$ is CH, $T^2$ and $T^3$ are N, X is $SO_2$, Q is phenyl;
(viv) G is N, $T^1$ is CH, $T^2$ and $T^3$ are N, X is $SO_2$, Q is heteroaryl; or
(vv) G is N, $T^1$ is CH, $T^2$ and $T^3$ are N, X is $SO_2$, Q is naphthyl;

In a further embodiment of the present invention there is provided a compound of formula Ia, or a pharmaceutically acceptable salt thereof, wherein:

G is selected from CH and N;

$T^1$ is selected from CH and N;

A is selected from a direct bond and (1–4C)alkylene;

T is selected from CH and N;

wherein the heterocyclic ring containing $T^1$ and the heterocyclic ring containing $T^2$ may, independently, be optionally substituted by one or more substituents selected from (1–6C)alkyl, (1–6C)alkoxy, phenyl(1–4C)alkyl, halogeno and (1–6C)alkoxycarbonyl;

X is selected from oxy, thio, sulphinyl, sulphonyl, carbonyl and methylene;

Q is selected from phenyl, naphthyl, phenyl(1–4C)alkyl and phenyl(2–6C)alkenyl, and wherein the last three groups may optionally bear a phenyl substituent;

and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cyclo alkyl(1–4C)alkyl, (1–4C)alkylenedioxy, (1–6C)alkylamino, di-[(n-6C)alkyl]amino, N-(1–6C)alkylcarbamoyl, di-N[(2–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl and tetrazolyl.

Particular, preferred and specific values include the appropriate values mentioned above.

In a particular group of compounds of formula Ia G is CH, $T^1$ is CH, $T^2$ is N, A is a direct bond or (1–4C)alkylene, X is selected from $CH_2$, CO, S, SO and $SO_2$, Q is selected from phenyl, naphthyl, phenyl (1–4C)alkyl and phenyl(2–6C) alkenyl, any of which may bear a phenyl substituent; and wherein a phenyl moiety in Q may be optionally substituted as hereinbefore defined, and wherein the heterocyclic rings containing $T^1$ and $T^2$ are optionally substituted as hereinbefore defined.

Particular, preferred and specific values include the appropriate values mentioned above.

In a further group of compounds of formula Ia G is CH or N, $T^1$ is CH, $T^2$ is N, A is a direct bond or (1–4C)alkylene, X is selected from $CH_2$, CO, $SO_2$ and S and Q is selected from phenyl and phenyl(2–6C)alkenyl; and wherein the heterocyclic rings containing $T^1$ and $T^2$ are each independently unsubstituted or bear one or two substituents selected from those hereinbefore defined and the phenyl moiety in Q is unsubstituted or bears one or two substituents independently selected from those hereinbefore defined.

In a further group of compounds of formula Ia G is CH or N, $T^1$ is N or CH (preferably CH), A is a direct bond, $T^2$ is N, X is $CH_2$, CO, or $SO_2$ and Q is phenyl, napthyl, phenyl(1–4C)alkyl, or phenyl(2–6C)alkenyl; and wherein the phenyl or naphthyl moiety in Q may be unsubstituted or may optionally bear one or two substituents selected from those hereinbefore defined.

Particular, preferred and specific values include the appropriate values mentioned above.

In a further group of compounds of formula Ia G is CH or N, $T^1$ is N or CH (preferably CH), A is a direct bond, $T^2$ is CH, X is S or CO and Q is phenyl or naphthyl; wherein the phenyl or naphthyl moiety in Q may be unsubstituted or may bear one or two substituents selected from those hereinbefore defined.

Particular, preferred and specific values include the appropriate values mentioned above.

In a further group of compounds of formula Ia G is CH or N, $T^1$ is CH, $T^2$ is CH or N (preferably N), A is a direct bond, Q—X— is selected from phenyl-$SO_2$—, phenyl-CH=$CHSO_2$—, napthyl-S—, benzyl- and napthyl-$SO_2$—; wherein the phenyl or naphthyl moiety may be unsubstituted or may optionally bear one or more (preferably one or two) substituents selected from those hereinbefore defined; and the heterocyclic rings containing $T^1$ and $T^2$ are unsubstituted.

In a further group of compounds of formula Ia G is N or CH, $T^1$ is CH, A is a direct bond or (1–2C)alkylene, $T^2$ is N, X is $CH_2$, S, CO or $SO_2$; and Q is selected from phenyl, naphthyl, phenyl(1–4C)alkyl and phenyl(2–6C)alkenyl, any of which may bear a phenyl substituent; and wherein a phenyl or naphthyl moiety in Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl and tetrazolyl; and the heterocyclic rings containing $T^1$ and $T^2$ are unsubstituted.

Particular, preferred and specific values include the appropriate values mentioned above.

As mentioned above, the present invention also provides a compound of formula I, or a pharmaceutically acceptable salt thereof, and a compound of formula Ia or a pharmaceutically acceptable salt thereof, as hereinbefore defined.

In particular there is provided a compound of formula I, or a pharmaceutically acceptable salt thereof, G is selected from CH and N;

$T^1$ is selected from CH and N;

$R^1$ is hydrogen, amino, halogeno, cyano, (1–6C)alkyl or (1–6C)alkoxy;

m is 1 or 2;

A is selected from a direct bond and (1–4C)alkylene;

$T^2$ is selected from CH and N;

$T^3$ is N;

a, b, c and d are each 2;

wherein the heterocyclic ring containing $T^1$ and the heterocyclic ring containing $T^2$ may, independently, be optionally substituted by one or more substituents selected from (1–6C)alkyl, (1–6C)alkoxy, phenyl(1–4C)alkyl, halogeno and (1–6C)alkoxycarbonyl;

X is selected from oxy, thio, sulphinyl, sulphonyl, carbonyl, carbonylamino, N-di-(1–6C)alkylcarbonylamnino, sulphonamido, methylene, (1–4C)alkymethylene and di-(1–6C)alkylmethylene, and when $T^2$ is CH, X may also be selected from aminosulphonyl and oxycarbonyl;

Q is selected from a heterocyclic moiety containing up to 4 heteroatoms selected from nitrogen, oxygen and sulphur; phenyl, naphthyl, phenyl(1–4C)alkyl and phenyl(2–6C)alkenyl, and wherein the last three groups may optionally bear a phenyl substituent; and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl, tetrazolyl and a heteroaryl group comprising a 5- or 6-membered monocyclic ring containing up to three heteroatoms selected from nitrogen, oxygen and sulphur.

Particular groups of compounds include the folowing in which G, a, b, c, d, $R^1$, m, $T^1$, $T^2$, $T^3$, X and Q may take any of the values mentioned above unless stated otherwise:

(i) G is CH; a, b, c and d are each 2; $T^1$ is CH, T and T are N, X is sulphonyl; Q is phenyl;

(ii) G is CH; a, b, c and d are each 2; $T^1$ is CH, $T^2$ and $T^3$ are N, X is sulphonyl; Q is naphthyl;

(iii) G is CH; a, b, c and d are each 2; $T^1$ is CH, $T^2$ and $T^3$ are N, X is sulphonyl; Q is heteroaryl;

(iv) G is CH; a, b, c and d are each 2; $T^1$ is CH, $T^2$ and $T^3$ are N, X is sulphonyl; Q is thienyl;

(v) G is N; a, b, c and d are each 2; $T^1$ is CH, $T^2$ and $T^3$ are N, X is sulphonyl; Q is phenyl;

(vi) G is N; a, b, c and d are each 2; $T^1$ is CH, $T^2$ and $T^3$ are N, X is sulphonyl; Q is naphthyl;

(vii) G is N; a, b, c and d are each 2; $T^1$ is CH, $T^2$ and $T^3$ are N, X is sulphonyl; Q is heteroaryl; or (viii) G is N; a, b, c and d are each 2; $T^1$ is CH, $T^2$ and $T^3$ are N, X is sulphonyl; Q is thienyl.

Compounds of particular interest are as follows in which G, a, b, c, d, $R^1$, m, $T^1$, $T^2$, $T^3$, X and Q may take any of the values mentioned above unless stated otherwise:

(i) G is CH; a, b, c and d are each 2; $T^1$ is CH, $T^2$ and $T^3$ are N, X is sulphonyl; Q is phenyl optionally substituted by one or more substituents selected from halogeno and (1–6C)alkyl;

(ii) G is CH; a, b, c and d are each 2; $T^1$ is CH, $T^2$ and $T^3$ are N, X is sulphonyl; Q is naphthyl optionally substituted by one or more substituents selected from halogeno and (1–6C)alkyl;

(iii) G is CH; a, b, c and d are each 2; $T^1$ is CH, $T^2$ and $T^3$ are N, X is sulphonyl; Q is heteroaryl optionally substituted by one or more substituents selected from halogeno and (1–6C)alkyl;

(iv) G is CH; a, b, c and d are each 2; $T^1$ is CH, $T^2$ and $T^3$ are N, X is sulphonyl; Q is thienyl optionally substituted by one or more substituents selected from halogeno and (1–6C)alkyl;

(v) G is N; a, b, c and d are each 2; $T^1$ is CH, $T^2$ and $T^3$ are N, X is sulphonyl; Q is phenyl optionally substituted by one or more substituents selected from halogeno and (1–6C)alkyl;

(vi) G is N; a, b, c and d are each 2; $T^1$ is CH, $T^2$ and $T^3$ are N, X is sulphonyl; Q is naphthyl optionally substituted by one or more substituents selected from halogeno and (1–6C)alkyl;

(vii) G is N; a, b, c and d are each 2; $T^1$ is CH, $T^2$ and $T^3$ are N, X is sulphonyl; Q is heteroaryl optionally substituted by one or more substituents selected from halogeno and (1–6C)alkyl; or (viii) G is N; a, b, c and d are each 2; $T^1$ is CH, $T^2$ and $T^3$ are N, X is sulphonyl; Q is thienyl optionally substituted by one or more substituents selected from halogeno and (1–6C)alkyl.

In general, it is preferred that the heterocyclic rings conating $T^1$ and $T^2/T^3$ are unsubstituted and:

(i) G is N; a, b, c and d are each 2; $T^1$ is CH, $T^2$ and $T^3$ are N, X is sulphonyl; Q is phenyl optionally substituted by one or more substituents independently selected from halogeno;

(ii) G is N; a, b, c and d are each 2; $T^1$ is CH, $T^2$ and $T^3$ are N, X is sulphonyl; Q is naphthyl optionally substituted by one or more substituents independently selected from halogeno;

(iii) G is N; a, b, c and d are each 2; $T^1$ is CH, $T^2$ and $T^3$ are N, X is sulphonyl; Q is heteroaryl optionally substituted by one or more substituents independently selected from halogeno; or (iv) G is N; a, b, c and d are each 2; $T^1$ is CH, $T^2$ and $T^3$ are N, X is sulphonyl; Q is thienyl optionally substituted by one or more substituents independently selected from halogeno.

Compounds of special interest include those described in the accompanying examples and their pharmaceutically acceptable salts and are hence provided as a further feature of the present invention.

The compounds of formula I and their pharmaceutically acceptable salts may be prepared by processes known to be applicable to the preparation of structurally related compounds. These procedures are illustrated by the following representative processes in which the various groups and radicals such as G, $T^1$, A, $T^2$, $T^3$, X and Q are as hereinbefore defined (unless stated otherwise), and are provided as a further feature of the present invention. In cases where the compounds contain a group such as an amino, hydroxy, or carboxy group, this group may be protected using a conventional protecting group which may be removed when desired by conventional means.

(a) When $T^3$ is N, reacting a compound of formula II, or a reactive derivative thereof, with an amine of formula III.

A suitable reactive derivative of an acid of formula II is, for example, an acyl halide such as an acyl chloride formed by the reaction of the acid with an inorganic acid chloride such as thionyl chloride. Further suitable reactive derivatives include a mixed anhydride such as an anhydride formed by the reaction of the acid with a chloroformate such as isobutyl chloroformate; an active ester such as an ester formed by the reaction of the acid and a phenol such as pentafluorophenol, an ester such as pentafluorophenyl trifluoroacetate or an alcohol such as N-hydroxybenzotriazole or N-hydroxysuccinimide; an acylazide, for example an azide formed by the reaction of the acid and an azide as dephenylphosphoryl azide; an acyl cyanide, for example a cyanide formed by the reaction of an acid and a cyanide such as diethylphosphoryl cyanide; or the product of the reaction of the acid and a carbodiimide such as N,N'-dicyclohexylcarbodiimide or N-(3-dimethylaminopropyl)-N'-ethylcarbodiimide.

The reaction is conveniently carried out in the presence of a suitable base such as, for example, an alkali or alkaline earth metal carbonate, alkoxide, hydroxide or hydride, for example sodium carbonate, potassium carbonate, sodium ethoxide, potassium butoxide, sodium hydroxide, potassium hydroxide, sodium hydride or potassium hydride, or an organometallic base such as an alkyl-lithium, for example n-butyl-lithium, or a dialkylamino-lithium, for example lithium di-isopropylamide, or, for example, an organic amine base such as, for example, pyridine, 2,6-lutidine, collidine, 4-dimethylaminopyridine, triethylamine, morpholine or diazabicyclo[5.4.0]undec-7-ene. The reaction is also preferably carried out in a suitable inert solvent or diluent, for example methylene chloride, chloroform, carbon tetrachloride, tetrahydrofuran, 1,2-dimethoxyethane, N,N-dimethylformamide, N,N-dimethylacetamide, N-methylpyrrolidin-2-one, dimethylsulphoxide or acetone, and at a temperture in the range, for example, −78° to 150° C., conveniently at or near ambient temperature.

A suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a tert-butyl group which may be removed, for example, by treatment with an acid, for example an oreganic acid such as trifluoroacetic acid, or for example a benzyl group which may be removed, for example, by hydrogenation over a catalyst such as palladium-on-carbon.

(b) For the preparation of compounds of formula I in which $T^2$ is N, reacting an amine of formula IV, with a compound of formula Z—X—Q in which Z is a displaceable group.

The reaction will, in general, be conveniently carried out in the presence of a suitable base. Suitable bases are those mentioned in (a) above.

A suitable value for the displaceable group Z is, for example, a halogeno or sulphonyloxy group, for example a fluoro, chloro, bromo, mesyloxy or 4-tolylsulphonyloxy group.

The reaction is conveniently performed in a suitable inert solvent or diluent as defined hereinbefore and at a temperature in the range, for example, 0° to 150° C., conveniently at or near ambient temperature.

(c) For the preparation of a compound of formula I in which $T^1$ is N, and wherein A is a direct bond, reacting a compound of formula V with an acid of formula $HO_2C$—X—Q or a reactive derivative thereof.

The reaction will, in general, be carried out in the presence of a suitable base as mentioned in (a) above.

The reaction is conveniently performed in a suitable inert solvent or diluent as defined hereinbefore and at a temperature in the range, for example 0° to 150° C., conveniently at or near ambient temperature.

(d) Reacting a compound of formula VI in which Z is a displaceable group with an amine of formula VII.

The reaction will, in general, be carried out in the presence of a suitable base as mentioned in (a) above.

Suitable values for Z are those mentioned in (b) above.

The reaction is conveniently carried out in a suitable inert solvent as mentioned in (a) above and at a temperature in the range, for example 0° C. to 150° C., conveniently in the range 15° C. to 100° C.

As mentioned above, it will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups are mentioned under (a) above. The protecting groups may be removed at any convenient stage in the synthesis using conventional techniques well known in the chemical art.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, allkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Fiedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

When an optically active form of a compound of the formula I is required, it may be obtained, for example, by carrying out one of the aforesaid procedures using an optically active starting material or by resolution of a racemic form of said compound using a conventional procedure.

As mentioned previously, the compounds of the formula I (and their pharmaceutically-acceptable salts) are inhibitors of the enzyme oxido-squalene cyclase. Thus, the compounds fo the present invention are capable or inhibiting cholesterol biosynthesis and hence in lowering choleserol levels in blood plasma.

The beneficial pharmacological properties of the compounds of the present invention maya be demonstrated using one or more of the following techniques.

(a) In vitro test to measure inhibition of oxido-squalene cyclase

This test measures the inhibition of microsomal oxido-squalene cyclase in vitro by compounds at set concentrations in the incubation medium.

Microsomes are prepared from rat liver according to methods known in the art, for example, the method described in published European Patent Application No 324,421 and stored in liquid nitrogen prior to assay. Assay vials are kept at 37° C. throughout the incubation. The microsomes typically contain 15–20 mg of protein per ml of microsomes. For assay, 1 ml of microsomes are diluted by the addition of 722 $\mu$l of 50 mM phosphate buffer pH 7.4.

Phosphate buffered Tween 80 (polyoxyethylene sorbitan monolaurate) is prepared by adding 0.1 g tween 80 to 100 ml of 50 mM phosphate buffer.

A stock solution of oxido-squalene is made up as a solution in ethanol (0.65 mg. ml.$^{-1}$). 18 $\mu$l of radio-labelled oxido-squalene (1 $\mu$Ci.ml$^{-1}$) is evaporated to dryness under a stream of nitrogen and redissolved in 1 ml of ethanol and 1 ml of the stock solution of oxido-squalene is added.

The test compound is dissolved in dimethyl sulphoxide to give a $10^{-4}$M stock solution. Dilutions are made from the stock to give $10^{-5}$M, $10^{-6}$M etc.

Phosphate buffered tween 80 (28 $\mu$l) is placed in 5 ml disposable plastic vials and 4 $\mu$l of the solution of the test compound is added and mixed well. An aliquot of the oxido-squalene mix (15 $\mu$l) is added and the vials pre-incubated for 10 minutes at 37° C. A portion of the microsomes (14.6 $\mu$l) are then added and incubated for a further 1 hour. The reaction is stopped by the addition of 315 $\mu$l of a mixture of 16% KOH in 20% ethanol.

The samples are then placed in a water bath at 80° C. for 2 hours to saponify. At the end of this process water (630 $\mu$l) is added followed by hexane (5 ml). The samples are tumble mixed for 5 minutes and then centrifuged. The hexane phase is removed and evaporated under nitrogen. The samples are then reconstituted in 300 $\mu$l of a 80:20 mixture of a acetonitrile:isopropyl alcohol. The samples are then chromatographed using a Hichrom 30DsS1 column with an isocratic elution using a 95:5 mixture of acetonitrile:isopropyl alcohol and a flow rate of 1 ml.min$^{-1}$. The output from the UV detector is connected to a radio-chemical detector to visualise radiolabelled sterols. Reaction rate is measured as the conversion of oxido-squalene to lanosterol, and the effects of test compounds are expressed as an inhibition of this process.

By way of example, the compound described in Example 10c gave an IC$_{50}$ of 81 nM.

(b) In vivo test to measure inhibition of oxido-squalene cyclase

The ability of a compound to inhibit oxido-squalene cyclase and/or inhibit cholesterol biosynthesis may be assessed by a routine laboratory procedure carried out in the rat. The test involves administration of the compound to rats on a reversed lighting regimen. Female rats (35–55 g) are housed in reverse lighting conditions (red light from 0200 h–1400 h) for a period of about 2 weeks prior to test. Animals are allowed free access to chow and drinking water throughout this period. At test, animals should weigh 100–140 g. The rats are dosed orally with the compound (typically 10–50 mg/kg) formulated in apolyethylene glycol/hydroxypropylmethyl cellulose mix. After 1 hour the rats are given triturated sodium mevalonate (15 $\mu$Ci/kg) intraperitoneally. Two hours after administration of the compound the rats are terminated and a piece of liver removed and weighed. The tissue is saponified at 80° C. for 2 hours in an ethanolic/potassium hydroxide solution (80% w/v aqueous KOH diluted 1:10 with ethanol). Water (2 ml) is added and the mixture extracted wiht iso-hexane (2>5 ml). The organic extracts are combined, evaporated to dryness under a stream of nitrogen and the residue is dissolved in a mixture of acetonitrile/iso-propanol (300 $\mu$l). An aliquot (200 $\mu$l) of this solution is loaded onto a HPLC column to separate the sterols. The radio-label content of each fraction is assessed using a radio chemical flow detector. Inhibitors of oxido squalene cyclase are classed as those compounds which caused a build up of substrate and a concomitant disappearance of cholesterol and its precursors. ED$_{50}$ values are generated in the usual manner.

By way of example, the compound described in Example 10c below gave 72% inhibition of cholesterol biosynthesis when dosed at 5 mg/kg.

No overt toxicity was detected when compounds of the formula I were adminstered at several multiples of their minimum inhibitory dose or concentration.

As mentioned previously, the compounds of the present invention are inhibitors of oxido-squalene cyclase and hence possess the property of inhibiting cholesterol biosynthesis. Thus the compounds of the present invention will be useful in treating diseases or medical conditions in which an inhibition of choleserol biosynthesis or lowering of cholesterol levels in blood plasma is desirable, for example, hypercholesterolemia and/or ischaemic diseases associated with atheromatous vascular degeneration such as atherosclerosis.

When used in the treatment of diseases and medical conditions such as those mentioned above it is envisaged that a compound of formula I, or a pharmaceutically acceptable salt thereof, will be administered orally, intravenously, or by some other medically acceptable route so that a dose in the general range of, for example, 0.01 to 10 mg per kg body weight is received. However it will be understood that the precise dose administered will necessarily vary according to the nature and severity of the disease, the age and sex of the patient being treated and the route of administration.

In general, the compounds of formula I, or a pharmaceutically-acceptable salt thereof, will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I, or a pharmaceutically-acceptable salt thereof, in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors, bile acid sequestrants, other hypocholesterolaemic agents such as fibrates, for example gemfibrozil, and drugs for the treatment of coronary heart disease.

As inhibitors of oxido-squalene cyclase, the compounds of the present invention may also find utility as antifungal agents, and so the present invention also provides a method of inhibiting cholesterol biosynthesis in fungi. In particular the present invention provides a method of treating fungal infections which comprises administration to a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

Compounds of formula I are described in published PCT patent application No.WO 96/10022. This reference also describes the prepartion of intermediates useful in the preparation of compounds of formula I in general and in particular to some of the compounds described below.

The invention will now be illustrated by the following non-limiting Examples in which, unless otherwise stated:
(I) evaporations were carried out by rotary evaporation in vacuo;
(ii) operations were carried out at room temperature, that is in the range 18–26° C.;
(iii) flash column chromatography or medium pressure liquid chromatography (MPLC) was performed on silica gel (Merck Kieselgel Art. 9385, obtained from E Merck, Darmstadt, Germany);
(iv) yields are given for illustration only and are not necessarily the maximum attainable by diligent process development;
(v) proton NMR spectra were normally determined at 200 MHz using tetramethylsilane (TMS) as an internal standard, and are expressed as chemical shifts (delta values) obtained in DMSO-$d_6$ (unless stated otherwise) in parts per million relative to TMS using conventional abbreviations for designation of major peaks: s, singlet; m, multiplet; t, triplet; br, broad; d, doublet;
(vi) all end-products were characterised by microanalysis, NMR and/or mass spectroscopy; and
(vii) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN acetonitrile, MeOH= methanol, EtOH=ethanol, $Pr^iOH$=2-propanol, $H_2O$= water.

EXAMPLE 1

3-Methyl-1-(2-naphthylsulphonyl)piperazine (1.8 g) and triethylamine (3.18 ml) were added in turn to a stirred solution of 1-(4-pyridyl)piperidine-4-carbonyl chloride (1.54 g) in methylene chloride (20 ml) and the mixture was stirred at ambient temperature for 16 hours. The mixture was partitioned between ethyl acetate and water. The organic phase was washed with water, dried ($MgSO_4$) and evaporated. The residue was purified by column chromatography using a 89:10:1 mixture of ethyl acetate; methanol and ammonia as eluent. The material so obtained was triturated under diethyl ether to give 3-methyl-1-(2-naphthylsulphonyl)-4-[1-(4-pyridyl)piperidin-4-yl-carbonyl]piperazine (32% yield);
NMR (100° C.): 1.5–1.75 (m, 4H), 2.45–2.7 (m, 3H), 3.19 (m, 1H), 3.57 (m, 1H), 3.75 (m, 3H), 4.06 (d, 1H), 4.52 (m, 1H), 6.65 (d, 2H), 7.6–7.79 (m, 3H), 8.0–8.15 (m, 5H), 8.38 (s, 1H); Microanalysis Found: C, 64.1; H, 6.4; N, 11.3; $C_{26}H_{30}N_4O_3S$ 0.25EtOAc 0.15$H_2O$ requires: C, 64.4; H, 6.47; N, 11.1%.

The 3-methyl-1-(2-naphthylsulphonyl)piperazine used as a starting material was obtained in quantitative yield by the reaction of 2-methylpiperazine and 2-naphthylsulphonyl chloride using an analogous procedure to that described in Example 2.

EXAMPLE 2

A solution of 2-naphthylsulphonyl chloride (0.55 g) in methylene chloride (10 ml) was added to a stirred mixture 1-[1-(4-pyridyl)piperidin-4-ylcarbonyl]piperazine trihydrochloride salt (0.85 g), triethylamine (3.1 ml) and methylene chloride (80 ml) and the resultant mixture was stirred at ambient temperature for 18 hours. The mixture was partitioned between methylene chloride and water. The organic phase was washed with water, dried ($MgSO_4$) and evaporated. The residue was purified by column chromatography using increasingly polar mixtures of methylene chloride and methanol (100:6 to 100:10) as eluent. There was thus obtained 1-(2-naphthylsulphonyl)-4-[1-(4-pyridyl) piperidin-4-ylcarbonyl]piperazine as a solid (0.727 g);
NMR: 1.4–1.65 (m, 4H), 2.75–3.05 (m, 7H), 3.5–3.7 (m, 4H), 3.8–3.95 (m, 2H), 6.8 (d, 2H), 7.65–7.8 (m, 3H), 8.05–8.25 (m, 5H), 8.45 (d, 1H); Microanalysis Found: C, 63.4; H, 6.1; N, 11.5%; $C_{25}H_{28}N_4O_3S$ 0.5$H_2O$ requires C, 63.4; H, 6.1; N, 11.8%.

The 1-[1-(4-pyridyl)piperidin-4-ylcarbonyl]piperazine used as a starting material was obtained as follows:

Thionyl chloride (1.6 ml) was added dropwise to a stirred suspension of 1-(4-pyridyl)piperidine-4-carboxylic acid (2.17 g) in methylene chloride (30 ml) and the mixture was stirred at ambient temperature for 1 hour. The mixture was evaporated to give 1-(4-pyridyl)piperidine-4-carbonyl chloride which was used without further purification.

The material so obtained was suspended in methylene chloride (30 ml) and triethylamine (7.8 ml) and a solution of 1-tert-butoxycarbonylpiperazine (2.08 g) in methylene chloride (10 ml) were added in turn. The mixture was stirred at ambient temperature for 4 hours. The mixture was partitioned between methylene chloride and water. The organic phase was washed with water, dried (MgSO$_4$) and evaporated. The residue was purified by column chromatography using increasingly polar mixtures of methylene chloride and methanol as eluent (100:5 to 100:13). There was thus obtained 1-(tert-butoxycarbonyl)-4-[1-(4-pyridyl)piperidin-4-ylcarbonyl]piperazine (2.38 g).

A saturated solution of hydrogen chloride in diethyl ether (25 ml) was added to a stirred solution of the 1-tert-butoxycarbonylpiperazine so obtained in methylene chloride (120 ml) and the mixture was stirred at ambient temperature for 18 hours. The mixture was evaporated and the residue was triturated under diethyl ether. There was thus obtained 1-[1-(4-pyridyl)piperidin-4-ylcarbonyl]piperazine trihydrochloride salt (2.85 g);
NMR: 1.5–1.9 (m, 4H), 3.0–3.2 (m, 7H), 3.6–3.85 (m, 4H), 4.15–4.3 (m, 2H), 7.2 (d, 2H), 8.2 (d, 2H).

EXAMPLE 3

The procedure described in Example 2 was repeated except that 8-chloronaphth-2-ylsulphonyl chloride was used in place of 2-naphthylsulphonyl chloride. There was thus obtained 1-(8-chloronaphth-2-ylsulphonyl)-4-[1-(4-pyridyl)piperidin-4-ylcarbonyl]piperazine in 74% yield;
NMR(CD$_3$SOCD$_3$+CD$_3$CO$_2$D): 1.35–1.7 (m, 4H), 2.85–3.15 (m, 7H), 3.5–3.7 (m, 4H), 3.95–4.1 (m, 2H), 7.0 (d, 2H), 7.75 (t, 1H), 7.85–7.95 (m, 2H), 8.1–8.2 (m, 3H), 8.3 (d, 1H), 8.55 (s, 1H); Microanalysis, Found: C, 59.4; H, 5.5; N, 10.9%; C$_{25}$H$_{27}$ClN$_4$O$_3$S 0.5H$_2$O requires: C, 59.1; H, 5.5; N, 11.0%.

EXAMPLE 4

Using an analogous procedure to that described in Example 2, 2-naphthylsulphonyl chloride was reacted with 3-ethoxycarbonyl-1-[1-(4-pyridyl)piperidin-4-ylcarbonyl]piperazine to give 2-ethoxycarbonyl-1-(2-naphthylsulphonyl)-4-[1-(4-pyridyl)piperidin-4-ylcarbonyl]piperazine in 31% yield;
NMR (100° C.): 1.05 (t, 3H), 1.5–1.8 (m, 4H), 2.9–3.25(m, 5H), 3.35–3.5 (m, 2H), 3.7–4.15 (m, 7H), 5.5–5.7 (m, 2H), 6.75–6.95 (m, 2H), 7.6–7.85 (m, 3H), 8.0–8.15 (m, 5H), 8.45 (d, 1H); Microanalysis, Found: C, 60.4; H, 6.1; N, 10.1%; C$_{28}$H$_{32}$N$_4$O$_5$S.H$_2$O requires C, 60.6; H, 6.1; N, 10.1%.

The 3-ethoxycarbonyl-1-[1-(4-pyridyl)piperidin-4-ylcarbonyl]piperazine used as a starting material was obtained as follows:

Using an analogous procedure to that described in Example 1, 1-(4-pyridyl)piperidine-4-carbonyl chloride was reacted with ethyl 1-benzylpiperazine-2-carboxylate (*Helv. Chim. Acta,* 1962, 45, 2383) to give 1-benzyl-2-ethoxycarbonyl-4-[1-(4-pyridyl)piperidin-4-ylcarbonyl]piperazine in 67% yield.

A mixture of the material so obtained (0.667 g), trifluoroacetic acid (2 ml), 10% palladium-on-carbon catalyst (0.15 g) and methanol (20 ml) was stirred under 7 atmospheres pressure of hydrogen for 48 hours. The mixture was filtered and evaporated. The residue was partitioned between methylene chloride and a saturated aqueous sodium bicarbonate solution. The organic phase was washed with water, dried (MgSO$_4$) and evaporated. The residue was triturated under diethyl ether to give the required starting material in quantitative yield;
NMR: 1.2–1.4 (m, 3H), 1.8–2.0 (m, 4H), 2.7–3.55 (m, 8H), 3.6–3.85 (m, 2H), 3.9–4.05 (m, 2H), 4.15–4.3 (m, 2H), 6.75 (d, 2H), 8.3 (d, 2H).

EXAMPLE 5

Using an analogous procedure to that described in Example 2, 1-[1-(4-pyridyl)piperidin-4-ylcarbonyl]piperazine was reacted with the appropriate (E)-styrenesulphonyl chloride. There was thus obtained the (E)-styrenes disclosed in Table I, the structures of which were confirmed by NMR spectroscopy. Unless otherwise stated, the appropriate (E)-styrenesulphonyl chlorides were obtained from the corresponding styrenes using an analogous procedure to that described in Note b. below Table I.

TABLE I

| Example 5 Compound No | R | m.p. (° C.) | Yield (%) |
|---|---|---|---|
| 1[a] | 4-methyl | 223–226 | 42 |
| 2[b] | 4-trifluoromethyl | foam | 30 |
| 3[c] | 2-methyl | 148–149 | 37 |
| 4[d] | 4-fluoro | 125–126 | 55 |
| 5[e] | 2-chloro | foam | 39 |
| 6[f] | 3,4-dichloro | foam | 33 |
| 7[g] | 4-bromo | foam | 54 |

Notes
[a] The product gave the following NMR signals: 1.4–1.85(m, 4H), 2.3(s, 3H), 2.95–3.3(m, 7H), 3.6(m, 4H), 4.07(m, 2H), 7.0(m, 3H), 7.25(m, 3H), 7.5(d, 2H), 8.05(d, 2H).
[b] The product gave the following NMR signals (CD$_3$SOCD$_3$ + CD$_3$CO$_2$D): 1.5–1.85(m, 4H), 3.0–3.3(m, 7H), 3.55–3.75(m, 4H), 4.15(m, 2H), 7.1(d, 2H), 7.5(m, 2H), 7.8(d, 2H), 7.95(d, 2H), 8.15(d, 2H).
[c] The product gave the following NMR signals: 1.45–1.75(m, 4H), 2.4(s, 3H), 2.85–3.25(m, 7H), 3.55–3.75(m, 4H), 3.92(m, 2H), 6.8(d, 2H), 7.1–7.4(m, 4H), 7.68(m, 2H), 8.15(d, 2H).
[d] The product gave the following NMR signals: 1.45–1.75(m, 4H), 2.85–3.0(m, 3H), 3.05–3.2(m, 4H), 3.5–3.75(m, 4H), 3.92(m, 2H), 6.85(d, 2H), 7.2–7.5(m, 4H), 7.85(m, 2H), 8.15(d, 2H).
[e] The product gave the following NMR signals: 1.45–1.75(m, 4H), 2.85–2.95(m, 3H), 3.05–3.25(m, 4H), 3.55–3.75(m, 4H), 3.92(m, 2H), 6.8 (d, 2H), 7.4–7.7(m, 5H), 8.0(m, 1H), 8.1(d, 2H).
[f] The product gave the following NMR signals (CD$_3$SOCD$_3$ + CD$_3$CO$_2$D): 1.5–1.9(m, 4H), 3.0–3.3(m, 7H), 3.55–3.75(m, 4H), 4.15(m, 2H), 7.1(d, 2H), 7.4(d, 2H), 7.7(m, 2H), 8.1(s, 1H), 8.15(d, 2H).
[g] The product gave the following NMR signals (CD$_3$SOCD$_3$ + CD$_3$CO$_2$D): 1.55–1.85(m, 4H), 3.0–3.35(m, 7H), 3.6–3.75(m, 4H), 4.17(m, 2H), 7.1(d, 2H), 7.15–7.5(m, 2H), 7.65(m, 4H), 8.15(d, 2H).

EXAMPLE 6

Using an analogous procedure to that described in Example 2, 1-[1-(4-pyridyl)piperidin-4-ylcarbonyl]piperazine was reacted with the appropriate 2-naphthalenesulphonyl chloride. There was thus obtained the compounds disclosed in Table II, the structures of which were confirmed by NMR spectroscopy. Unless otherwise stated, the appropriate naphthylsulphonyl chlorides were obtained from the corresponding naphthalenes using an analogous procedure to that described in Note b. below Table III in Example 7.

TABLE II

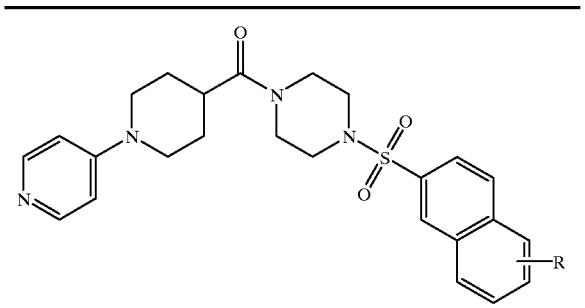

| Example 6 Compound No | R | m.p. (° C.) | Yield |
|---|---|---|---|
| 1[a] | 7-ethoxy | glass | 13 |
| 2[b] | 6-chloro | 115 (decomposes) | 82 |
| 3[c] | 6-bromo | 142–145 | 81 |
| 4[d] | 6-methoxy | gum | 28 |
| 5[e] | 6-fluoro | 108–111 (decomposes) | 73 |

Notes
[a] The product gave the following NMR signals: 1.35–1.7(m, 4H), 1.45(t, 3H), 2.8–3.05(m, 7H), 3.3(m, 2H), 3.5–3.7(m, 4H), 3.83(m, 2H), 4.2(m, 2H), 6.85(d, 2H), 7.35(m, 1H), 7.58(m, 2H), 7.95–8.15(m, 4H), 8.3(d, 1H).
[b] The product gave the following NMR signals (CD$_3$SOCD$_3$ + CD$_3$CO$_2$D): 1.45–1.8(m, 4H), 2.9–3.1(m, 5H), 3.22(m, 2H), 3.55–3.75(m, 4H), 4.1(m, 2H), 7.05(d, 2H), 7.65–7.85(m, 2H), 8.1–8.25(m, 5H), 8.45(s, 1H); and the following analytical data: Found C, 58.9; H, 5.3; N, 10.9%; C$_{25}$H$_{27}$ClN$_4$O$_3$S 0.2CH$_2$Cl$_2$ requires: C, 58.7; H, 5.3; N, 10.9%.

The 6-chloro-2-naphthylsulphonyl chloride used as a starting material was obtained as follows:

A solution of sodium nitrite (2.7 g) in water (5 ml) was added during 2 hours to a stirred mixture of 6-amino-2-naphthalenesulphonic acid (8.8 g), dilute aqueous hydrochloric acid (2.8% weight/volume, 20 ml) and water (15 ml) which had been cooled to 0° C. The mixture was stirred at 0° C. for 30 minutes and then poured onto a stirred suspension of cuprous chloride (3.96 g) in dilute aqueous hydrochloric acid (2.8%, 20 ml). The mixture was stored at ambient temperature for 18 hours. The mixture was evaporated to give 6-chloro-2-naphthalenesulphonic acid which was used without further purification.

The material was suspended in DMF (40 ml) and cooled to 5° C. Thionyl chloride (8.6 ml) was added dropwise and the mixture was stirred at 5° C. for 3 hours. The mixture was poured onto ice and extracted with methylene chloride. The organic solution was dried (MgSO$_4$) and evaporated. The residue was purified by column chromatography using a 20:1 mixture of hexane and ethyl acetate as eluent. There was thus obtained 6-chloro-2-naphthylsulphonyl chloride (2.49 g); NMR: 7.45 (m, 1H), 7.8 (m, 1H), 7.85 (d, 1H), 8.05 (m, 2H), 8.2 (s, 1H).
c. The product gave the following NMR signals: 1.35–1.65 (m, 4H), 2.75–3.05 (m, 7H), 3.5–3.7 (m, 4H), 3.87 (m, 2H), 6.8 (d, 2H), 7.85 (m, 2H), 8.05–8.25 (m, 4H), 8.4 (d, 1H), 8.5 (d, 1H).

The 6-bromo-2-naphthylsulphonyl chloride used as a starting material was obtained in 22% yield from 6-amino-2-naphthalenesulphonic acid using an analogous procedure to that described in Note e above except that hydrobromic acid and cuprous bromide were used in place of hydrochloric acid and cuprous chloride respectively. The material gave the following NMR signals: 7.65 (m, 1H), 7.75–8.0 (m, 3H), 8.15–8.2 (m, 2H).
d. The product gave the following NMR signals (100° C.): 1.48–1.73 (m, 4H), 2.75–3.02 (m, 3H), 3.06–3.11 (t, 4H), 3.56 (t, 4H), 3.76 (t, 1H), 3.81 (t, 1H), 3.95 (s, 3H), 6.7 (d, 2H), 7.32 (m, 1H), 7.44 (m, 1H), 7.71 (m, 1H), 8.03 (m, 2H), 8.12 (d, 2H), 8.31 (d, 1H).

The 6-methoxy-2-naphthylsulphonyl chloride used as a starting material was obtained as follows:

A mixture of sodium 6-hydroxy-2-naphthylsulphonate (5 g) and DMSO (100 ml) was added to a stirred suspension of sodium hydride (60% dispersion in mineral oil, 1 g) in DMSO (20 ml) and the mixture was stirred at ambient temperature for 30 minutes. The mixture was cooled to 10° C. and methyl iodide (22 ml) was added dropwise. The mixture was allowed to warm to ambient temperature and was stirred for 2 hours. The mixture was poured into acetone and the precipitate was isolated and washed in turn with acetone and diethyl ether. There was thus obtained sodium 6-methoxy-2-naphthylsulphonate (3.3 g).

Thionyl chloride (0.82 ml) was added to a stirred solution of a portion (0.96 g) of the material so obtained in DMF (10 ml). The mixture was stirred at ambient temperature for 2 hours. The mixture was poured onto ice. The precipiate was isolated and dried. There was thus obtained 6-methoxy-2-naphthylsulphonyl chloride (0.7 g) which was used without further purification.

e. The product gave the following NMR signals (CD$_3$SOCD$_3$+CD$_3$CO$_2$D): 1.45–1.8 (m, 4H), 2.9–3.1 (m, 5H), 3.22 (m, 2H), 3.55–3.75 (m, 4H), 4.12 (m, 2H), 7.1 (d, 2H), 7.57 (m, 1H), 7.75–7.9 (m, 2H), 8.15 (m, 2H), 8.3 (m, 1H), 8.5 (d, 1H).

The 6-fluoro-2-naphthylsulphonyl chloride used as a starting material was obtained as follows:

6-Amino-2-naphthalenesulphonic acid (5.41 g) was added portionwise during 10 minutes to a stirred suspension of nitrosonium tetrafluoraborate (3.12 g) in methylene chloride (100 ml) which had been cooled to 5° C. The mixture was stirred at 5° C. for 2 hours and at ambient temperature for 18 hours. The mixture was evaporated and 1,2-dichlorobenzene (100 ml) was added to the residue. The mixture was stirred and heated to 150° C. for 2 hours. The mixture was cooled to 5° C. and thionyl chloride (3.6 ml) and DMF (10 ml) were added. The mixture was stirred at ambient temperature for 18 hours. The mixture was partitioned between methylene chloride and water. The organic phase was dried (MgSO$_4$) and evaporated. The residue was purified by column chromatography using a 9:1 mixture of hexane and ethyl acetate as eluent. There was thus obtained 6-fluoro-2-naphthylsulphonyl chloride (1.53 g); NMR: 7.4 (m, 1H), 7.65–7.9 (m, 3H), 8.05 20 (m, 2H), 8.2 (d, 1H).

EXAMPLE 7

Using an analogous procedure to that described in Example 2, 1-[1-(4-pyridyl)piperidin-4-ylcarbonyl] piperazine was reacted with the appropriate benzenesulphonyl chloride. There were thus obtained the compounds disclosed in Table III, the structures of which were confirmed by NMR spectroscopy.

TABLE III

[Structure shown: pyridyl-piperidine-carbonyl-piperazine-sulfonyl-phenyl-R]

| Example 7 Compound No | R | m.p. (° C.) | Yield (%) |
|---|---|---|---|
| 1[a] | 4-bromo | glass | 67 |
| 2[b] | 4-(4-chlorophenyl) | glass | 61 |

Notes

[a] The product gave the following NMR signals: 1.4–1.7(m, 4H), 2.8–3.0 (m, 7H), 3.5–3.7(m, 4H), 3.8–3.95(m, 2H), 6.75(d, 2H), 7.65(d, 2H), 7.85 (d, 2H), 8.12(broad s, 2H).

[b] The product gave the following NMR signals ($CD_3SOCD_3$ + $CD_3CO_2D$): 1.55–1.8(m, 4H), 2.8–3.05(m, 3H), 3.15(t, 4H), 3.6(t, 4H), 3.85(m, 2H), 6.75(d, 2H), 7.55(d, 2H), 7.75(d, 2H), 7.9(d, 2H), 8.15(d, 2H).

The 4'-chloro-4-biphenylylsulphonyl chloride used as a starting material was obtained as follows:

Chlorosulphonic acid (9 ml) was added dropwise to a stirred solution of 4-chlorobiphenyl (21 g) in chloroform (200 ml) and the mixture was stirred at ambient temperature for 30 min. The precipitate was isolated and washed with chloroform (50 ml). There was thus obtained 4'-chloro-4-biphenylylsulphonic acid (26.8 g).

Thionyl chloride (0.85 ml) was added dropwise to a stirred solution of 4'-chloro-4-biphenylylsulphonic acid (1.7 g) in DMF (120 ml) which had been cooled to 5° C. The mixture was stirred at ambient temperature for 3 hours. The mixture was poured into water and the resultant precipitate was isolated, dissolved in diethyl ether, dried ($MgSO_4$) and re-isolated by evaporation of the solvent. There was thus obtained 4'-chloro-4-biphenylylsulphonyl chloride (0.7 g) which was used without further purification.

EXAMPLE 8

Using an analogous procedure to that described in Example 2 except that DMF was used in place of methylene chloride as the reaction solvent, 1-($^2$-[4-(4-pyridyl) piperazin-1-yl]acetyl)piperazine was reacted with 2-naphthylsulphonyl chloride to give 1-(2-naphthylsulphonyl)-4-(2-[4-pyridyl)piperazin-1-yl]acetyl) piperazine in 22% yield;

NMR ($CD_3SOCD_3$+$CD_3CO_2D$): 2.4–2.5 (m, 4H), 2.9–3.05 (m, 4H), 3.15 (s, 2H), 3.3–3.45 (m, 4H), 3.45–3.65 (m, 4H), 6.95 (d, 2H), 7.5–7.75 (m, 3H), 7.95–8.2 (m, 5H), 8.4 (s, 1H); Microanalysis, Found: C, 62.1; H, 6.1; N, 14.4%; $C_{25}H_{29}N_5O_3S$ requires: C, 62.6; H, 6.1; N, 14.6%.

The 1-(2-[4-(4-pyridyl)piperazin-1-yl]acetyl)piperazine used as a starting material was obtained as follows:

N,N'-Dicyclohexylcarbodiimide (0.84 g) was added to a stirred mixture of 2-[4-(4-pyridyl)piperazin-1-yl]acetic acid (1 g), 1-(tert-butoxycarbonyl)piperazine (0.67 g), N-hydroxybenzotriazole (0.382 g), N-methylmorpholine (0.79 ml) and DMF (30 ml) which had been cooled to 5° C. The mixture was stirred at ambient temperature for 18 hours. The mixture was evaporated and the residue was purified by column chromatography using a 17:3 mixture of methylene chloride and methanol as eluent. There was thus obtained 1-(tert-butoxycarbonyl)-4-(2-[4-(4-pyridyl)piperazin-1-yl] acetyl)piperazine as a foam (0.87 g).

A mixture of a portion (0.75 g) of the material so obtained, trifluoroacetic acid (2 ml) and methylene chloride (5 ml) was stirred at ambient temperature for 4 hours. The mixture was evaporated to give 1-(2-[4-(4-pyridyl)piperazin-1-yl]acetyl) piperazine in quantitative yield;

NMR: 3.05–3.25 (m, 4H), 3.55–3.7 (m, 2H), 3.7–3.8 (m, 2H), 3.9–4.1 (m, 4H), 4.3 (s, 2H), 7.3 (d, 2H), 8.4 (d, 2H), 9.35 (s, 2H).

EXAMPLE 9

A mixture of succinimido 1-(4-pyrimidinyl)piperidine-4-carboxylate (0.326 g), 1-[(E)-4-chlorostyrylsulphonyl] piperazine (0.4 g) and DMF (5 ml) was stirred at ambient temperature for 16 hours. The mixture was partitioned between ethyl acetate and water. The organic phase was washed with water, dried ($MgSO_4$) and evaporated. The residue was purified by column chromatography using a 49:1 mixture of methylene chloride and methanol as eluent. The material so obtained was recrystallised from acetonitrile. There was thus obtained 1-[(E)4-chlorostyrylsulphonyl]-4-[1-(4-pyrimidinyl)piperidin-4-ylcarbonyl]piperazine (0.133 g, 22%), m.p. 209–210° C.;

NMR: 1.3–1.6 (m, 2H), 1.7 (m, 2H), 2.9–3.2 (m, 7H), 3.5–3.8 (m, 4H), 4.4 (m, 2H), 6.8 (d, 1H), 7.4 (m, 4H), 7.8 (d, 2H), 8.15 (d, 1H), 8.45 (s, 1H); microanalysis, found: C, 55.2; H, 5.5; N, 14.7%; $C_{22}H_{26}ClN_5O_3S$ requires: C, 55.5; H, 5.5; N, 14.7%.

The succinimido 1-(4-pyrimidinyl)piperidine-4-carboxylate used as a starting material was obtained as follows:

4-Chloropyrimidine hydrochloride was reacted with ethyl piperidine-4-carboxylate to give ethyl 1-(4-pyrimidinyl) piperidine-4-carboxylate in 46% yield. A mixture of the material so obtained (0.5 g), 2N aqueous hydrochloric acid (5 ml) and THF (15 ml) was stirred and heated to reflux for 18 hours. The mixture was evaporated and the residue was washed with ethyl acetate. There was thus obtained 1-(4-pyrimidinyl)piperidine-4-carboxylic acid hydrochloride salt (0.49 g, 95%);

NMR: 1.6 (m, 2H), 2.0 (m, 2H), 2.7 (m, 1H), 3.4 (m, 2H), 4.5 (broad s, 2H), 7.2 (d, 1H), 8.3 (d, 1H), 8.8 (s, 1H).

A mixture of the acid so obtained, N-hydroxysuccinimide (0.29 g), triethylamine (0.61 g), N-(3-dimethylaminopropyl)-N'-ethylcarbodiimide (0.48 g) and DMSO (10 ml) was stirred at ambient temperature for 5 hours. The mixture was partitioned between ethyl acetate and water. The organic phase was washed with water, dried ($MgSO_4$) and evaporated. There was thus obtained succinimido 1-(4-pyrimidinyl)piperidine-4-carboxylate which was used without further purification.

The 1-[(E)-4-chlorostyrylsulphonyl)piperazine used as a starting material was obtained in 42% yield by the reaction of piperazine and (E)-4-chlorostyrylsulphinyl chloride using an analogous procedure to that described in Example 2.

EXAMPLE 10

Using an analogous precedure to that described in Example 1, 1-(4-pyridylpiperidine-4-carbonyl chloride was reacted with the appropriate 1-(phenylsulphonyl)piperazine. There was thus obtained the compounds disclosed in Table IV, the structures of which were confirmed by NMR spectroscopy.

TABLE IV

| Example 10 Compound No. | R | m.p. (° C.) | Yield (%) |
|---|---|---|---|
| 1[a] | 4-(4-bromophenyl) | 203–207 | 54 |
| 2[b] | 4-(3,5-dichlorophenyl) | gum | 13 |
| 3[c] | 4-iodo | glass | 79 |

Notes

[a] The product gave the following NMR signals (CD$_3$SOCD$_3$ + CD$_3$CO$_2$D): 1.6–1.85(m, 4H), 2.98(m, 1H), 3.05–3.3(m, 6H), 3.55–3.65(m, 4H), 3.93 (m, 2H), 6.9(d, 2H), 7.55–7.65(m, 4H), 7.8–7.9(m, 4H), 8.1(d, 2H).
The 1-(4'-bromobiphenyl-4-ylsulphonyl)piperazine used as a starting material was obtained from 4-bromobiphenyl. That compound was converted into 4'-bromo-4-biphenylylsulphonyl chloride using analogous procedures to those described in Note b below Table III in Example 7. The material so obtained was reacted with piperazine using an analogous procedure to that described in Example 2. The required starting material gave the following NMR signals: 2.7–2.8(m, 4H), 2.8–2.9(m, 4H), 7.75(d, 4H), 7.8(d, 2H), 7.95(d, 2H).
[b] The product gave the following NMR signals: 1.5–1.75(m, 4H), 2.8–3.15 (m, 7H), 3.55–3.65(m, 4H), 3.8(m, 2H), 6.7(d, 2H), 7.55(t, 1H), 7.7(d, 2H), 7.8–7.95(m, 4H), 8.1(d, 2H).
The starting material 1-(3',5'-dichlorobiphenyl-4-ylsulphonyl)piperazine gave the following NMR signals: 2.7–2.8(m, 4H), 2.8–2.9(m, 4H), 7.65(t, 1H), 7.75–7.85(m, 4H), 8.0(d, 2H).
[c] The product gave the following NMR signals: 1.41–1.64(m, 4H), 2.82–2.91(m, 7H), 3.53–3.62(m, 4H), 3.89(d, 2H), 6.78(d, 2H), 7.49(d, 2H); 8.02(d, 2H), 8.10(d, 2H).

EXAMPLE 11

Using an analogous procedure to that described in Example 1, 1-(4-pyridyl)piperidine-4-carbonyl chloride was reacted with ethyl 1-(6-chloronaphth-2-ylsulphonyl) piperazine-3-carboxylate to give 4-(6-chloronaphth-2-ylsulphonyl)-2-ethoxycarbonyl-1-[1-(4-pyridyl)piperidin-4-ylcarbonyl]piperazine in 37% yield;
NMR (100° C.): 1.2 (t, 3H), 1.5–1.8 (m, 4H), 2.6 (m, 1H), 2.8 (m, 1H), 2.85–3.05 (m, 4H), 3.65–3.85 (m, 3H), 4.05–4.25 (m, 4H), 5.1 (m, 1H), 6.7 (d, 2H), 7.65 (m, 1H), 7.8 (m, 1H), 8.1–8.25 (m, 5H), 8.45 (d, 1H); microanalysis, found: C, 58.5; H, 5.6; N, 9.6%; C$_{28}$H$_{31}$ClN$_4$O$_5$S requires: C, 58.9; H, 5.5; N, 9.8%.

EXAMPLE 12

Using an analogous procedure to that described in Example 1, 1-(4-pyridyl)piperidine-4-carbonyl chloride was reacted with 2-benzyl-1-(2-naphthylsulphonyl)piperazine to give 2-benzyl-1-(2-naphthylsulphonyl)4-[1-(4-pyridyl) piperidin-4-ylcarbonyl]piperazine in 70% yield; m.p. 186–188° C.;
NMR: 1.6 (m, 4H); 2.7 (m, 3H); 3.0 (m, 4H), 3.9 (m, 4H), 4.2 (d, 2H), 6.6 (d, 3H), 7.2 (d, 5H), 7.7 (m, 3H), 8.1 (m, 5H), 8.5 (s, 1H). Microanalysis, found: C, 67.9; H, 6.3; N, 9.8%; C$_{32}$H$_{34}$N$_4$O$_3$S 0.6H$_2$O requires: C, 68.0; H, 6.3; N, 9.9%.

The 2-benzyl-1-(2-naphthylsulphonyl)piperazine used as a starting material was obtained as follows:

N-Methylmorpholine (3.12 ml) was added to a stirred mixture of N-tert-butoxycarbonyl-DL-phenylalanine (3 g), N-benzylglycine ethyl ester (2.18 g), N-hydroxybenzotriazole (1.26 g) and DMF (50 ml) which had been cooled to 0° C. The mixture was stirred at 0° C. for 30 minutes and at ambient temperature for 16 hours. The mixture was filtered and the filtrate was evaporated. The residue was partitioned between ethyl acetate and water. The organic phase was washed with water, dried (MgSO$_4$) and evaporated. The residue was purified by column chromatography using a 5:1 mixture of hexane and ethyl acetate as eluent to give a solid (3.7 g).

A mixture of the material so obtained and a 4M solution of hydrogen chloride in diethyl ether was stirred at ambient temperature for 16 hours. The mixture was evaporated to give phenylalanyl-N-benzylglycine ethyl ester (2.65 g); NMR: 1.2 (m, 2H), 3.1 (t, 2H), 3.6 (m, 4H), 4.1 (m, 2H), 4.6 (m, 2H), 7.2 (m, 1OH), 8.4 (s, 2H).

A mixture of a portion (0.5 g) of the material so obtained, N-methylmorpholine (0.15 g) and a 0.1 M solution of acetic acid in c-butanol (25 ml) was stirred and heated to reflux for 3 hours. The mixture was evaporated and the residue was partitioned between methylene chloride and water. The organic phase was washed with water, dried (MgSO$_4$) and evaporated. The residue was purified by column chromatography using increasingly polar mixtures of methylene chloride and methanol as eluent. There was thus obtained 1,3-dibenzyl-2,5-dioxopiperazine (0.29 g), m.p. 173–174° C.

After repetition of the previous reaction, a mixture of 1,3-dibenzyl-2,5-dioxopiperazine (1.6 g), boron trifluoride diethyl ether complex (0.1 g) and THF (5 ml) was stirred and heated to reflux for 15 minutes. The mixture was cooled to ambient temperature and borane dimethyl sulphide complex (0.04 ml) was added dropwise. The mixture was stirred at ambient temperature for 30 minutes. The mixture was evaporated and the residue was heated to 100° C. for 5 minutes. A 6N aqueous hydrochloric acid solution (1 ml) was added and the mixture was heated to reflux for 1 hour. The mixture was cooled to 0° C. and a 6N aqueous sodium hydroxide solution (1.5 ml) was added. The mixture was partitioned between methylene chloride and a saturated aqueous potassium carbonate solution. The organic phase was washed with water, dried (MgSO$_4$) and evaporated. The residue was purified by column chromatography using increasingly polar mixtures of methylene chloride and methanol as eluent. There was thus obtained 1,3-dibenzylpiperazine (0.29 g).

A solution of the material so obtained in methylene chloride (3 ml), was added dropwise to a stirred mixture of 2-naphthylsulphonyl chloride (0.257 g), triethylamine (0.7 ml) was methylene chloride (5 ml) which had been cooled to 0° C. The mixture was stirred at ambient temperature for 16 hours. The mixture was evaporated and the residue was partitioned between methylene chloride and water. The organic phase was washed with water, dried (MgSO$_4$) and evaporated. The residue was purified by column chromatography using increasingly polar mixtures of methylene chloride and methanol as eluent. There was thus obtained 2,4-dibenzyl-1-(2-naphthylsulphonyl)piperazine (0.37 g); NMR: 1.8 (m, 2H), 2.6 (m, 3H), 3.1 (m, 2H), 3.45 (d, 1H), 3.75 (d, 1H), 4.1 (s, 1H), 6.95 (m, 2H), 7.1 (m, 3H), 7.25 (s, 5H), 7.75 (m, 3H), 8.1 (m, 3H), 8.5 (s, 1H).

A mixture of the material so obtained, 10% palladium-on-carbon catalyst (0.23 g) and methylene chloride (50 ml) was stirred under an atmosphere of hydrogen for 24 hours.

The mixture was filtered and the filtrate was evaporated. The residue was purified by column chromatography using a 99:1 mixture of methylene chloride and methanol as eluent. There was thus obtained 2-benzyl-1-(2-naphthylsulphonyl)piperazine (0.08 g).

NMR: 2.4–2.8 (m, 4H), 3.1–3.4 (m, 3H), 3.6 (d, 1H), 4.0 (t, 1H), 7.2 (m, 5H), 7.7 (m, 3H), 8.1 (m, 3H), 8.4 (s, 1H).

EXAMPLE 13

A mixture of 1-(4-pyridyl)piperazine (0.163 g)and 4-nitrophenyl-4-(6-chloronaphth-2-ylsulphonyl)piperazine-1-carboxylate (0.475 g) in DMF (5 ml) was stirred and heated to 100° C. for 16 hours. The mixture was evaported and the residue was partitioned between ethyl acetate and 2N aqueous hydrochloric acid. The aqueous layer was basified by the addition of dilute aqueous sodium hydroxide solution and the mixture was extracted with ethyl acetate. The organic extract was dried ($MgSO_4$) and evaporated. The solid so obtained was recrystallised from a mixture of isohexane and ethyl acetate. There was thus obtained 1-(6-chloronaphth-2-ylsulphonyl)-4-[4-(4-pyridyl)piperazin-1-ylcarbonyl)piperazine (0.34 g); NMR: 2.95–3.05 (m, 4H), 3.15–3.3 (m, 12H), 6.75(m, 2H), 7.75 (m, 1H), 7.8 (m, 1H), 8.1–8.3 (m, 5H), 8.5 (s, 1H); Microanalysis, found: C, 57.5; H, 5.3; N, 13.9%; $C_{24}H_{26}ClN_5O_3S$ requires: C, 57.7; H, 5.2; N, 14.0%.

The 4-nitrophenyl 4-(6-chloronaphth-2-ylsulphonyl) piperazine-1-carboxylate used as a starting material was obtained as follows:

A solution of 4-nitrophenyl chloroformate (0.4 g) in methylene chloride (15 ml) was added to a stirred mixture of 1-(6-chloronaphth-2-ylsulphonyl)piperazine hydrochloride salt (0.69 g), triethylamine (0.56 ml) and methylene chloride (30 ml) which had been cooled to 0° C. The mixture was stirred at ambient temperature for 16 hours. The mixture was evaporated and the residue was partitioned between ethyl acetate and a concentrated aqueous sodium bicarbonate solution. The organic solution was washed with 1N aqueous hydrochloric acid solution and with water, dried ($MgSO_4$) and evaporated. The solid so obtained was recrystallised from a mixture of isohexane and ethyl acetate. There was thus obtained 4-nitrophenyl 4-(6-chloronaphth-2-ylsulphonyl)piperazine-1-carboxylate (0.73 g); NMR: 3.1 (m, 4H), 3.5–3.75 (m, 4H), 7.25 (m, 1H), 7.38 (d, 2H), 7.85(m, 1H), 8.15–8.3 (m, 5H), 8.5 (s, 1H).

EXAMPLE 14

Using an analogous procedure to that described in Example 1, 1-(4-pyridyl)piperidine-4-carbonyl chloride was reacted with 4-(2-naphthylthio)piperidine to give 4-(2-naphthylthio)-1-[1-(4-pyridyl)piperidin-4-ylcarbonyl] piperidine in 62% yield; NMR (100° C.): 1.25–1.75 (m, 6H), 1.87–2.1 (brs, 2H), 2.78–3.0 (m, 4H), 3.20 (d, 1H), 3.64 (m, 1H), 3.6–4.04 (m, 3H), 4.2 (d, 1H), 6.78 (d, 2H), 7.44–7.58 (m, 3H), 7.63–7.74 (m, 3H), 7.75 (d, 1H), 8.12 (s, 2H); Microanalysis found: C, 72.2; H, 6.7; N, 9.7%; $C_{26}H_{29}N_3OS$ requires: C, 72.4; H, 6.8; N, 9.7%.

The 4-(2-naphthylthio)piperidine used as a starting material was obtained as follows:

A solution of 2-naphthalenethiol (2.34 g) in DMF (10 ml) was added dropwise to a stirred mixture of sodium hydride (60% dispersion in mineral oil, 0.65 g) and DMF (20 ml) which had been cooled to 10 C. The resultant mixture was stirred at 0° C. for 30 minutes. A solution of tert-butyl 4-mesyloxypiperidine-1-carboxylate (3.9 g) in DMF (40 ml) was added dropwise. The mixture was allowed to warm to ambient temperature. The mixture was partitioned between ethyl acetate and water. The organic phase was washed with water, dried ($MgSO_4$) and evaporated. The residue was purified by column chromatography using methylene chloride as eluent. There was thus obtained tert-butyl 4-(2-naphthylthio)piperidine-1-carboxylate (0.65 g).

A mixture of the material so obtained and trifluoroacetic acid was stirred at ambient temperature for 30 minutes. The mixture was diluted with ethyl acetate and washed with 2N aqueous sodium hydroxide solution. The organic solution was dried ($MgSO_4$) and evaporated. There was thus obtained 4-(2-naphthylthio)piperidine (0.32 g);
NMR: 1.42 (m, 2H), 1.88 (m, 2H), 2.58 (m, 2H), 2.94 (m, 2H), 3.43 (m, 1H), 7.5 (m, 3H), 7.89 (m, 4H).

EXAMPLE 15

To a solution of 1-(4-pyridyl)piperazine (357 mg), 1-hydroxybenztriazole (300 mg), N-methylmorpholine (0.36 ml) and N-(2-sulphonylnaphthylene)nipecotic acid (700 mg) in DMF (20 ml), cooled to 0° C., was added 1,3-dicyclohexylcarbodiimide (70 mg). The resulting mixture was allowed to warm to room temperature and stirred for 18 hours. The mixture was concentrated and purified by flash column chromatography on silica eluting with methanol/methylene chloride (8:92 v/v) to give 1-(2-naphthylsulphonyl)-3-(1-(4-pyridyl)piperidin-4-ylcarbonyl) piperidine (250 mg) as a white foam;
NMR: 0.95–1.75 (m, 6H), 2.3–2.45 (m, 2H), 2.55–2.65 (m, 1H), 3.5–3.75 (m, 8H), 7.05 (d, 2H); 7.6–7.75 (m, 3H); 8.0–8.2 (m, 5H); 8.4 (s, 1H).

The N-(2-sulphonylnaphthylene)nipecotic acid used as a starting material was obtained as follows:

Triethylamine (4 ml) was added to a solution of 2-naphthylenesulphonyl chloride (1.45 g) in methylene chloride (10 ml), cooled to 5° C., followed by a solution of ethyl nipecotate (1 g) in methylene chloride (5 ml). The mixture was allowed to warm to ambient temperature and stirred for 18 hours. The mixture was concentrated and purified by flash column chromatography on silica eluting with ethyl acetate/hexane (35:65 v/v) to give ethyl N-(2-sulphonylnaphthylene) nipecotate (1.38 g) as a white solid;
NMR: 1.1 (t, 3H); 1.45–1.7 (m, 2H); 1.8–2.0 (m, 2H), 2.25–2.55 (m, 3H), 3.55–3.65 (m, 2H), 4.0 (q, 2H), 7.65–7.8 (m, 3H), 8.05–8.25 (m, 3H), 8.45 (d, 1H).

A mixture of potassium hydroxide (430 mg) in ethanol (12 ml) was added to a solution of ethyl N-(2-sulphonylnaphthylene) nipecotate (1.33 g) in ethanol (5 ml). The resulting mixture was refluxed at 80° C. for 4 hours. The mixture was evaporated to dryness and dissolved in water (5 ml) and acidified with 2N HCl. The precipitate was filtered and washed with water (5 ml) to give N-(2-sulphonylnaphthylene)nipecotic acid (810 mg):
NMR: 1.45–1.64(m, 2H), 1.8–1.95(m, 2H), 2.15–2.35(m, 1H), 2.4–2.6(m, 2H), 3.5–3.65(m, 2H), 7.65–7.8(m, 3H), 8.05–8.25(m, 3H), 8.45(d, 1H).

EXAMPLE 16

A suspension of 1-(4-pyridyl)piperidine-4-carbonyl chloride (0.94 g) in dichloromethane (20 ml) was added slowly to a stirred solution of 4-(4-bromophenoxy)piperidine (1.0 g) and triethylamine (1.09 ml) in dichloromethane (10 ml) at 5° C. under an atmosphere of argon. The mixture was stirred at ambient temperature for 16 hours, and then the solvent was removed by evaporation. The residue was triturated with water. The resulting solid was collected by filtration and recrystallised from ethanol (10 ml) to give 4-(4-bromophenoxy)-1-[1-[4-pyridyl]piperidin-4-ylcarbonyl] piperidine (0.58 g) as an off-white solid, m.p. 127–130° C.; NMR: 1.4–1.8 (m, 6H), 1.8–2.1 (m, 2H), 2.8–3.1 (m, 3H), 3.1–3.5(m, 2H), 3.7–4.0(m, 4H), 6.7–6.9(br, 2H), 6.9–7.0(d, 2H), 7.4–7.5(d, 2H) and 7.9–8.3(br, 2H); Microanalysis, found: C, 58.0; H, 6.2; N, 9.2%; $C_{22}H_{26}BrN_3O_2$ 0.6 $H_2O$ requires: C, 58.1; H, 6.0; N, 9.2%; MS: m/z 444(M+H).

EXAMPLE 17

A suspension of 1-(4-pyridyl)piperidine-4-carbonyl chloride (1.68 g) in dichloromethane (40 ml) was added slowly to a stirred solution of 4-(4-bromothiophenoxy)piperidine (1.90 g) and triethylamine (1.94 ml) in dichloromethane (20 ml) at 5–10° C. under an atmosphere of argon. The mixture was stirred at ambient temperature for 16 hours and then the solvent was removed by evaporation. The residue was partitioned between water (100 ml) and ethyl acetate (100 ml, 70 ml, 70 ml). The ethyl acetate extracts were combined, washed successively with saturated sodium hydrogen carbonate solution and brine, dried ($Na_2SO_4$) and evaporated. The residual oil was purified by flash column chromatography on silica gel using a mixture of 1% aqueous ammonia (density, 0.88 g/cm³) solution/ethyl acetate as eluent. The purified product (0.5 g) was then dissolved in ethanol (10 ml) and treated with a solution of hydrogen chloride gas in ethanol to give pH2. The solid was collected by filtration and washed with ether to give 4-(4-bromothiophenoxy)-1-[1-[4-pyridyl]piperidin-4-yl)carbonyl]piperidine hydrochloride (0.37 g) as a colourless solid, m.p. 195–198° C.;
NMR: 1.2–1.7(m, 4H), 1.7–1.85(m, 2H), 1.8–2.05(m, 2H), 2.7–2.95(m, 1H), 3.0–3.2(m, 1H), 3.1–3.35(m, 3H), 3.45–3.6(m, 1H), 3.94.05(m, 1H), 4.1–4.3(d, 3H), 7.1–7.2(d, 2H), 7.3–7.4(d, 2H), 7.5–7.6(d. 2H), 8.15–8.25(d, 2H), and 12.5–14.5(br, 1H); microanalysis, found: C, 51.9; H, 5.8; N, 8.2%; $C_{22}H_{26}BrN_3OS.HCl$ 0.7$H_2O$ requires: C, 51.9; H, 5.6; N, 8.3%; MS: m/z 460(M+H).

The 4-(4-bromothiophenoxy)piperidine used as starting material was prepared as follows:

Methane sulphonyl chloride (7.5 ml) was added over a period of 1.5 hours to an ice-cooled solution of 1-t-butoxycarbonyl-4-hydroxypiperidine (5.0 g) and triethylamine (17.3 ml) in dry dichloromethane (100 ml) under an atmosphere of argon so that the temperature of the mixture was maintained at 2 to 4° C. The mixture was stirred at 5° C. for a further 1 hour, then at ambient temperature for 16 hours. The mixture was poured into water (300 ml) and extracted with dichloromethane (3×100 ml). The dichloromethane extracts were combined, washed successively with saturated aqueous sodium carbonate and brine, dried ($Na_2SO_4$) and evaporated. The residue was purified by suction chromatography on silica gel using a mixture of 10% ethyl acetate/dichloromethane as eluent. The purified product was triturated with n-pentane to give 1-t-butoxycarbonylpiperidine-4-methane sulphonate (6.2 g) as a pale orange solid, m.p. 91–93° C.;
NMR ($CDCl_3$): 1.43–1.47(s, 9H), 1.7–2.05(m, 4H), 3.00–3.03(s, 3H), 3.23–3.35(m, 2H), 3.65–3.77(m, 2H), and 4.82–4.93(m, 1H); MS: m/z 280 ((M+H).

A solution of 4-bromothiophenol (9.1 g) in dry dimethylformamide (20 ml) was added dropwise over 30 minutes to a stirred suspension of sodium hydride (60% W/w dispersion in mineral oil, 2.0 g) in dry dimethylformamide (15 ml) under an atmosphere of argon, whilst maintaining the temperature of the mixture at 0 to 2° C. using an ice-methanol bath. The mixture was stirred for 25 minutes at 2° C.

A solution of 1-t-butoxycarbonylpiperidine-4-methane sulphonate (6.1 g) in dry dimethylformamide (20 ml) was added over 5 minutes to the stirred, ice-cooled mixture. The mixture was stirred at 5° C. for 1 hour and then at ambient temperature for 16 hours.

The solution was poured into water (600 ml) and extracted with ethyl acetate (4×200 ml). The ethyl acetate extracts were combined, washed with water (4×150 ml), dried ($Na_2SO_4$) and evaporated. The residue was purified by flash column chromatography on silica gel using dichloromethane as eluent to give 4-(4-bromothiophenoxy)-1-t-butoxycarbonylpiperidine (5.3 g) as a solid, m.p. 62–65° C.;
NMR ($CDCl_3$): 1.4–1.5(s, 9H), 1.45–1.6(m, 2H), 1.8–1.95 (m, 2H), 2.85–3.0(m, 2H), 3.1–3.25(m, 1H), 3.85–4.05(m, 2H), 7.2–7.3(d, 2H) and 7.35–7.45(d, 2H): Microanalysis, found: C, 51.5; H, 6.0; N, 3.7%; $C_{16}H_{22}BrNO_2S$ requires: C, 51.6; H, 6.0; N, 3.8%;

Trifluoroacetic acid (7.5 ml) was added in portions to a stirred, ice-cooled solution of 4-(4-bromothiophenoxy)-1-t-butoxycarbonylpiperidine (2.6 g) in dry dichloromethane (5 ml) under an atmosphere of argon so that the temperature of the mixture was maintained between 5 and 10° C. The solution was stirred at 5° C. for 1 hour, then at ambient temperature for 2 hours. The solution was evaporated. The residual oil was treated with a saturated aqueous solution of sodium carbonate and extracted with ethyl acetate (3×70 ml). The ethyl acetate extracts were combined, dried ($Na_2SO_4$) and evaporated. The residue was purified by flash column chromatography on silica gel, using a mixture of 95:5:3, ethyl acetate:methanol:aqueous ammonia (density 0.88 g/cm³) as eluent, to give 4-(4-bromothiophenoxy) piperidine (1.9 g) as an off-white solid;
NMR ($CDCl_3$): 1.4–1.6 (m, 2H), 1.85–2.0 (m, 2H), 2.55–2.7 (m, 2H), 3.05–3.2 (m, 3H), 7.2–7.3 (d, 2H) and 7.35–7.45 (d. 2H); MS: m/z 272 (M+H).

EXAMPLE 18

A mixture of 1-[1-(4-pyridyl)piperidin-4-yl carbonylpiperazine (274 mg) and triethylamine (285 μl) in methylene chloride (5 ml) was added to a solution of 3,5-dimethyl-4-fluorobenzenesulphonyl chloride (245 mg) in methylene chloride (5 ml) and the resultant mixture stirred at ambient temperature for 18 hours. The methylene chloride solution was washed with water (5 ml), saturated sodium carbonate solution (2×5 ml) water (5 ml) and evaporated. There was thus obtained 1-(3,5-dimethyl-4-fluorobenzenesulphonyl)-4-[1-(4-pyridyl)piperidin-4-yl carbonyl]piperazine as a solid (379 mg);

HPLC system
Column Highchrome Hirpb
Flow Rate 1.0–1.5 ml/min
Detector Wavelength 215λ
Oven Temperature 40° C.
Solvent A 0.1% TFA/$H_2O$
Solvent B 0.1% TFA/$CH_3CN$

| Time | % Solvent A | % Solvent B | Flow Rate |
|---|---|---|---|
| 0 | 95 | 5 | 1.5 ml/min |
| 3 | 95 | 5 | 1.5 ml/min |
| 17 | 5 | 95 | 1.5 ml/min |
| 18 | 95 | 5 | 1.5 ml/min |
| 20 | 95 | 5 | 1.5 ml/min |

HPLC purity = 87%
Retention time = 13.03 minutes

EXAMPLE 19

Using an analogous procedure to that described in Example 18 but using 4-fluorobenzene sulphonyl chloride as starting material in place of 3,5-dimethyl-4-fluorobenzenesulphonyl chloride, there was obtained 1-(4-fluorobenzenesulphonyl)-4-[1-(4-pyridyl)piperidin-4-yl carbonyl]piperazine as a solid (286 mg);
HPLC purity=92%
Retention time=11.76 minutes

EXAMPLE 20

Using an analogous precedure to that described in Example 2, 1-[1-(4-pyridyl)piperidin-4-ylcarbonyl] piperazine was reacted with the appropriate sulphonyl chloride of formula Q'—SO$_2$Cl to give the compounds listed below in Table V.

TABLE V

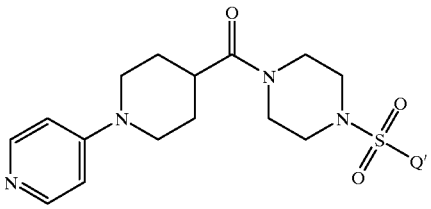

| Compound No. | Q' | Yield | NMR |
|---|---|---|---|
| 1 | 5-dimethyl-amino-naphth-1-yl | 61% | 1.53–1.78(m, 4H), 2.67–3.07(m, 9H), 3.19–3.28(t, 4H), 3.5–3.60(t, 4H), 3.74–3.85(dt, 2H), 6.68–6.74(dd, 2H), 7.28–7.35(d, 1H), 7.58–7.63(d, 1H), 7.63–7.70(d, 2H), 8.10–8.20(m, 3H), 8.32–8.40(d, 1H), 8.55–8.63(d, 1H). |
| 2 | 2,4,6-trimethyl-phenyl | 82% | [a] 1.70–1.95(m, 4H), 2.30(s, 3H), 2.6 (s, 6H), 2.96–3.10(m, 1H), 3.10–3.20(t, 4H), 3.23–3.40(m, 2H), 3.54–3.65(t, 4H), 3.94–4.10(dt, 2H), 6.98–7.08(m, 4H), 8.05–8.15(d, 2H). |
| 3 | 2-nitro-phenyl | 68% | 1.38–1.75(m, 4H), 2.75–3.01(m, 3H), 3.01–3.40(m, 4H), 3.40–3.78(m, 4H), 3.78–4.0(m, 2H), 6.68(d, 2H), 7.80–8.03 (m, 4H), 8.03–8.20(m, 2H). |
| 4 | phenyl | 32% | [a] 1.50–1.85(m, 4H), 2.85–3.1(br.m, 5H), 3.15–3.35(m, 2H), 3.50–3.75(m, 4H), 4.05–4.22(m, 2H), 7.05–7.15(d, 2H), 7.54–7.84(m, 5H), 8.07–8.20(d, 2H). |
| 5 | 5-chloro-naphth-2-yl | 61% | [b] 1.65–2.0(m, 4H), 2.55–2.7(m, 1H), 2.8–2.95(m, 2H), 3.05–3.2(m, 4H), 3.6–3.95(m, 6H), 6.65(d, 2H), 7.6(t, 1H), 7.95–8.0(m, 3H), 8.25(d, 2H), 8.35(d, 1H), 8.45(d, 1H). |
| 6 | 4-phenyl-phenyl | 64% | 1.35–1.7(m, 4H), 2.8–3.0(m, 7H), 3.5–3.7(m, 4H), 3.8–3.95(m, 2H), 6.8(d, 2H), 7.4–7.6(m, 3H), 7.7–7.85(m, 4H), 7.95(d, 2H), 8.1(d, 2H). |

Notes:
[a] d$^6$-DMSO/CD$_3$CO$_2$D
[b] CDCl$_3$

EXAMPLE 21

Using an analogous procedure to that described in Example 1, 1-(4-pyridyl)piperidine-4-carbonyl chloride was reacted with the appropriate piperazine derivative to give the compounds listed in Table VI.

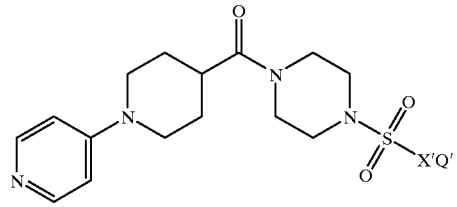

TABLE VI

| Compound No | X' | Q' | Yield | NMR |
|---|---|---|---|---|
| 1 | SO$_2$ | 3-bromo phenyl | 19% | 1.58–1.83 (m, 4H), 2.88–3.04 (m, 1H), 3.04–3.15 (t, 4H), 3.15–3.32 (m, 2H), 3.53–3.64 (t, 4H), 3.89–4.03 (dd, 2H), 6.90–7.0 (d, 2H), 7.48–7.58 (t, 1H), 7.70–7.78 (dd, 1H), 7.78–7.89 (m, 2H), 8.02–8.14 (d, 2H). |
| 2 | CO | 2-naphthyl | 10% | 1.47–1.78 (m, 4H), 2.80–3.05 (m, 3H), 3.40–3.80 (m, 8H), 3.85–4.02 (m, 2H), 6.72–6.86 (d, 2H), 7.50–7.67 (m, 3H), 7.97–8.06 (m, 4H), 8.05–8.22 (m, 2H). |
| 3 | CH$_2$ | phenyl | 77% | 1.5–1.75 (m, 4H), 2.25–2.45 (m, 4H), 2.8–3.0 (m, 3H), 3.4–3.6 (m, 6H), 3.85–4.0 (m, 2H), 6.8 (d, 2H), 7.25–7.4 (m, 5H), 8.15 (d, 2H). |

The piperazine derivatives were prepared by reaction of the appropriate piperazine with the appropriate phenylsulphonyl chloride, naphthylsulphonyl chloride or benzyl chloride in quantitative yield. Structures were confirmed by NMR spectroscopy.

EXAMPLE 22

Using an analogous procedure to that described in Example 1, 1-(4-pyridyl)piperidine-4-carbonyl chloride was reacted with 1-[4-(2-pyridyl)phenylsulphonyl]piperazine to give 1-[4-(2-pyridyl)phenyl-sulphonyl]4-[1(4-pyridyl) piperidine-4-ylcarbonyl]piperazine in 54% yield, m.p. 224–226° C.;
NMR: 1.35–1.65 (m, 4H), 2.75–3.05 (m, 7H), 3.5–3.7 (m, 4H), 3.88 (m, 2H), 6.75 (d, 2H), 7.45 (m, 1H), 7.8–8.0 (m, 3H), 8.05–8.15 (m, 3H), 8.35 (d, 2H), 8.72 (m, 1H); Microanalysis, found C, 62.7; H, 5.9; N, 14.0%; $C_{26}H_{29}N_5O_3S$ 0.5$H_2O$ requires C, 62.4; H, 6.0; N, 14.0%.

The 1-[4-(2-pyridyl)phenylsulphonyl]piperazine used as a starting material was obtained as follows:

A mixture of 1-(4-iodophenylsulphonyl)piperazine (0.48 g), (2-pyridyl)tributyltin (1.18 g), tetrakis(triphenylphosphine)palladium(0) (0.1 g) and toluene (15 ml) was stirred and heated to reflux for 18 hours. The mixture was evaporated and the residue was purified by column chromatography using increasingly polar mixtures of methylene chloride and methanol as eluent. There was thus obtained 1-[4-(2-pyridyl)phenylsulphonyl]piperazine (0.439 g);
NMR: 2.65–2.8 (m, 4H), 2.8–2.9 (m, 4H), 7.45 (m, 1H), 7.8–8.1 (m, 3H), 8.35 (d, 2H), 8.73 (m, 1H).

EXAMPLE 23

A mixture of 2-amino-4-chloro-6-methylpyrimidine (0.143 g), 1-(2-naphthylsulphonyl)-4-(4-piperidinylcarbonyl)piperazine (0.387 g), triethylamine (0.101 g) and ethanol (5 ml) was stirred and heated to reflux for 18 hours. The mixture was cooled to ambient temperature and partitioned between ethyl acetate and water. The organic phase was washed with water, dried ($MgSO_4$) and evaporated. The residue was triturated under diethyl ether. There was thus obtained 4-[1-(2-amino-6-methylpyrimidin-4-yl)piperidin-4-ylcarbonyl]-1-(2-naphthylsulphonyl) piperazine (0.29 g, 58%);
NMR: 1.2–1.45 (m, 2H), 1.55 (m, 2H), 2.05 (s, 3H), 2.8 (m, 3H), 2.9–3.2 (m, 4H), 3.5–3.7 (m, 4H), 4.23 (m, 2H), 5.95 (d, 3H), 7.7–7.85 (m, 3H), 8.2 (m, 3H), 8.45 (s, 1H); Microanalysis, found C, 60.1; H, 6.4; N, 16.6%; $C_{25}H_{30}N_6O_3S$ 0.3$H_2O$ requires C, 60.1; H, 6.1; N, 16.8%.

EXAMPLE 24

Using an analogous procedure to that described in Example 23, 2-amino-4-chloropyrimidine was reacted with 1-(6-chloronaphth-2-ylsulphonyl)-4-(4-piperidinylcarbonyl)piperazine. The precipitate which was deposited on cooling the reaction mixture was isolated, washed with cold ethanol and dried. There was thus obtained 4-[1-(2-aminopyrimidin-4-yl)piperidin-4-ylcarbonyl]-1-(6-chloronaphth-2-ylsulphonyl)piperazine in 73% yield, m.p. 265–267° C.;
NMR: 1.0–1.4 (m, 4H), 2.5–2.7 (m, 3H), 2.7–2.9 (m, 4H), 3.3–3.5 (m, 4H), 4.08 (m, 2H), 5.7 (s, 2H), 5.8 (d, 1H), 7.5–7.7 (m, 3H), 7.75 (d, 1H), 8.05 (s, 1H), 8.1 (d, 1H), 8.3 (s, 1H); Microanalysis, found C, 55.9; H, 5.4; N, 15.9%; $C_{24}H_{27}ClN_6O_3S$ requires C, 56.0; H, 5.3; N, 16.3%.

EXAMPLE 25

4-Chloropyrimidine (1.72 g) and triethylamine (5.3 ml) were added to a solution of 4-(1-(6-chloronaphth-2-ylsulphonyl)piperazin-4-ylcarbonyl)piperidine (4 g) in ethanol (100 ml) and the mixture heated on a steam bath overnight. The mixture was cooled to give a precipitate which was collected to filtration and recrystallised from acetonitrile to give 1-(6-chloronaphth-2-ylsulphonyl)-4-[1-[4-pyrimidinyl]piperidin-4-ylcarbonyl]piperazine (2.88 g); mp 218–219° C.;
NMR: 1.25–1.5 (m, 2H), 1.53–1.7 (m, 2H), 2.8–3.1 (m, 7H), 3.5–3.75 (m, 4H), 4.25–4.4 (m, 2H), 6.75 (dd, 1H), 7.7 (dd, 1H), 7.85 (dd, 1H), 8.15 (d, 1H), 8.2 (d, 1H), 8.25–8.3 (m, 3H), 8.45(s, 1H), 8.5 (s, 1H).

The starting material was prepared as follows:

N-Hydroxysuccinimide (25.3 g) was added to a solution of 1-(t-butoxycarbonyl)piperidine-4-carboxylic acid (45.8 g) in DMF (250 ml) and the mixture stirred at 5° C. EDAC (42 g) was added and the mixture stirred for 4 hours at 5° C. A further portion of EDAC (5.73 g) was added and the mixture allowed to warm to ambient temperature and stirred overnight. The mixture was evaporated to half its original volume and the residue partitioned between ethyl acetate (1000 ml) and water (250 ml). The ethyl acetate phase was separated, washed with water (2×250 ml), brine (50 ml), dried ($MgSO_4$) and evaporated to give a solid which was recrystallised from a mixture of ethyl acetate/hexane (250 ml/500 ml) to give 1-(1-(t-butoxycarbonyl)piperidin-4-ylcarbonyloxy)2,5-dioxopyrrolidine (55 g);
NMR ($CDCl_3$): 1.45 (s, 9H), 1.7–2.1 (m, 4H), 2.7–3.1(m, 7H), 3.9–4.1(m, 2H).

Triethylamine (2.92 ml) was added to a mixture of 1-(6-chloronaphth-2-ylsulphonyl)piperazine hydrochloride (6.93 g) in dichloromethane (100 ml). 1-(1-(t-butoxycarbonyl) piperidin-4-ylcarbonyloxy)-2,5-dioxopyrrolidine (6.25 g) was added and the mixture stirred overnight. The mixture was evaporated to give a solid which was suspended in ethyl acetate (200 ml). Water (50 ml) was added and the ethyl acetate phase separated, washed with water (4×50 ml), brine (50 ml), dried ($MgSO_4$) and evaporated. The residue was purified by flash chromatography on silica gel using a 75:25 mixture of ethyl acetate/hexane as eluent to give 1-(t-butoxycarbonyl)-4-(1-(6-chloronaphth-2-ylsulphonyl) piperazin-4-ylcarbonyl)piperidine (8.1 g);
NMR: 1.12–1.6 (m, 13H), 2.6–2.8 (m, 3H), 2.9–3.05 (m, 4H), 3.5–3.7 (m, 4H), 3.8–3.9(m, 2H), 7.7(dd, 1H), 7.8(dd, 1H), 8.15(d, 1H), 8.75–8.35(m, 3H), 8.3(s, 1H).

1-(t-Butoxycarbonyl)4-(1-(6-chloronaphth-2-ylsulphonyl)piperazin-4-ylcarbonyl)piperidine (28 g) was added in portions with stirring to trifluoroacetic acid (100 ml). The mixture was stirred for one hour. The trifluoroacetic acid was removed by evaporation. Aqueous 2M sodium hydroxide solution (150 ml) was added to the residue and the mixture extracted with dichloromethane (500 ml). The dichloromethane extract was washed with aqueous 2M sodium hydroxide solution (2×50 ml), water (2×100 ml), dried ($MgSO_4$) and evaporated to give a solid which was recrystallised from a mixture of ethyl acetate/hexane to give 4-(1-(6-chloronaphth-2-ylsulphonyl)piperazin-4-ylcarbonyl)piperidine (20.31 g);
NMR ($CDCl_3$): 1.5–1.75 (m, 4H), 2.4–2.7 (m, 3H), 3.0–3.2 (m, 6H), 3.5–3.75 (m, 4H), 7.55 (dd, 1H), 7.75 (dd, 1H), 7.9–8.0 (m, 3H), 8.3 (s, 1H).

EXAMPLE 26

Dicyclocarbodiimide (620 mg) was added to a stirred mixture of the crude 3-carboxy-1-[4-pyridylpiperidin-4-ylcarbonyl]piperidine product from step (b) (1 g), aniline (0.17 ml), hydroxybenztriazole, (236 mg), N-methylmorpholine (0.29 ml) under an atmosphere of argon with cooling to 0 to 5° C. The mixture was stirred at 0° C. for 30 minutes and then allowed to warm to ambient temperature and stirred overnight. The mixture was quenched with water and the solvent removed by evaporation. The residue was partitioned between dichloromethane and water. The aqueous phase was seperated and washed with dichloromethane. The aqueous phase was evaporated and the residue purified by flash chromatography on silica gel using 15% MeOH/CHCl$_2$ as eluent to give a crude product which was further purified by flash chromatography on silica gel using a gradient of 4 to 10% MeOH/CH$_2$Cl$_2$ as eluent to give an oil. Ether was added and then evaporated to yield 3-(phenylaminocarbonyl)-1-[1-(4-pyridyl)piperidin-4-ylcarbonyl]piperidine as a foam (200 mg; 80% pure);

NMR: 1.6–1.9 (m, 8H), 2.0 (m, 2H), 3.2 (m, 4H), 3.9–4.5 (m, 4H), 7.0 (m, 3H), 7.2 (q, 2H), 7.5 (t, 2H), 8.1 (d, 2H).

The starting material was prepared as follows:

Thionyl chloride (5.6 ml) was added to a solution of pyridyl piperidine carboxylic acid (8 g) in dichloromethane (100 ml) under an atmosphere of argon. The mixture was stirred for 2 hours. The thionyl chloride and solvent were removed by evaporation. Dichloromethane (100 ml) was added and the mixture cooled to 0° C. Triethylamine (21.7 ml) was added to the mixture whilst cooling in an ice-bath followed by ethyl nipecotate (6.03 ml). The mixture was allowed to warm to ambient temperature and then stirred overnight. The solvent was removed by evaporation and the residue purified by flash chromatography on silica gel using a gradient of 5 to 15% MeOH/CH$_2$Cl$_2$ as eluent. The crude product was partitioned between water and dichloromethane. The organic extract was washed with water (×2), brine, dried (MgSO$_4$) and evaporated. The residue was purified further by flash chromatography on silica gel using a gradient of 0 to 5% MeOH/CH$_2$Cl$_2$ as-eluent to give 3-ethoxycarbonyl-1-[4-pyridylpiperidin-4-ylcarbonyl]piperidine (5.3 g);

NMR: 1.2 (m, 3H), 1.4–1.8 (m, 8H), 2.0 (m, 2H), 2.9 (t, 4H), 3.9 (t, 4H), 4.1 (m, 2H), 6.8 (d, 2H), 8.1 (s, 2H); MS: M/z 347 (M+H).

A mixture of 3-ethoxycarbonyl-1-[4-pyridylpiperidin-4-ylcarbonyl]piperidine (5.27 g), potassium hydroxide (1.71 g) and ethanol (40 ml) was heated at 80° C. for 4 hours. The mixture was allowed to cool and filtered. The filtrate was evaporated and acidified to pH 2 using aqueous 2M hydrochloric acid. The mixture was evaporated to give a solid which was used without further purification (assumed to be 60% pure by weight);

NMR (CD$_3$SOCD$_3$+CD$_3$CO$_2$D): 1.5–2.0 (m, 8H), 2.0 (m, 2H), 3.0–3.4 (m, 2H), 3.9 (d, 2H), 4.2 (d, 4H), 7.1 (d, 2H), 8.1 (d, 2H), MS: m/z 318.

EXAMPLE 27

Thionyl chloride (0.73 ml) was added to a stirred mixture of pyridyl piperidine carboxylic acid (0.83 g) in dichloromethane (20 ml) under an atmosphere of argon. The mixture was stirred for 2 hours. The excess thionyl chloride and dichloromethane were removed by evaporation. The residue was stirred in dichloromethane (30 ml) under Argon and cooled to 0° C. Triethylamine (3.5 ml) was added to the ice-cooled mixture followed by 4-(phenylmethylaminocarbonyl)piperidine. The mixture was allowed to warm to ambient temperature and stirred overnight. The solvent was removed by evaporation and water was added to the residue. The aqueous mixture was extracted with dichloromethane (×3). The dichloromethane extracts were combined and evaporated. The residue was purified by flash chromatography on silica gel using dichloromethane containing increasing amount of methanol (5 to 15% MeOH/CH$_2$Cl$_2$) as eluent to give 4-(phenylmethylaminocarbonyl)-1-(1-(4-pyridyl)piperidin-4-ylcarbonyl)piperidine as a foam (260 mg);

NMR: 1.6–1.9 (m, 8H), 2.7 (m, 2H), 3.2 (m, 2H), 3.4 (t, 2H), 4.1–4.5 (m, 6H), 7.1–7.4 (m, 7H), 8.2 (d, 2H), 8.4 (t, 1H), MS: m/z 407 (M+H).

The starting material was prepared as follows:

Sodium carbonate (2.48 g) was added to a stirred mixture of isonipecotic acid (3.0 g), water (30 ml) and dioxan (30 ml) under an atmosphere of argon whilst cooled in an ice/salt bath. Boc-O-Boc (5.09 g) was added and the mixture allowed to warm to ambient temperature. The mixture was stirred overnight. The mixture was concentrated to a third of its original volume by evaporation. Ethyl acetate was added followed by saturated potassium hydrogen sulphate solution to give a pH of 2 to 3. The mixture was extracted with ethyl acetate (×3). The extracts were combined, washed with water, brine, dried (MgSO$_4$) and evaporated to give a solid (4.63 g);

NMR (CDCl$_3$): 1.5 (s, 9H), 1.7 (m, 2H), 1.8 (2d, 2H), 2.5 (m, 1H), 2.8 (m, 2H), 4.1 (d, 2H); MS: m/z 230.

Dicyclocarbodiimide (1.02 g) was added to a stirred mixture of the product thus obtained (1 g), benzylamine (0.53 ml), hydroxy benzotriazole (590 mg), N-methylmorpholine (0.96 ml) and dimethylformamide (30 ml) under an atomosphere of argon with cooling to 0 to 5° C. The mixture was stirred at 0° C. for 30 minutes and then allowed to warm to ambient temperature and stirred overnight. The mixture was quenched with water and the solvent removed by evaporation. The residue was purified by flash chromatography on silica gel using 70% EtoAc/hexane as eluent to give a gum (1.16 g);

NMR: 1.4 (s, 9H), 1.5 (2d, 2H), 1.7 (2d, 2H), 2.4 (m, 1H), 2.7 (t, 2H), 4.0 (m, 2H), 4.3 (d, 2H), 7.3 (m, 5H), 8.3 (t, 1H).

A mixture of the product thus obtained (1.1 g), dichloromethane (10 ml) and trifluoroacetic acid (2.5 ml) was stirred overnight. The trifluoroacetic acid and dichloromethane were removed by evaporation to give a residue which was further evaporated under a high vacuum to give 4-(benzamido)piperidine as a viscous liquid which was used without further purification;

NMR: 1.8 (m, 4H), 2.5 (m, 1H), 2.8 (q, 2H), 3.3 (d, 2H), 4.3 (d, 2H), 7.3 (m, 5H), 8.4 (s, 1H).

EXAMPLE 28

1-(1-(4-pyridyl)piperdin-4-ylcarbonyl)piperazine (0.411 g) was dissolved in dry dichloromethane (20 mL) and stirred under argon at 0° C. To the resulting solution was added triethylamine (0.56 mL) followed by the dropwise addition of a solution of 4-cyanobenzenesulphonyl chloride (0.33 g, 1.6 mmol) in dry pyridine (20 mL). The reaction was then stirred at 0° C. for 10 minutes and then allowed to warm to room temperature and stirred for a further 1 hour. The reaction was quenched by the removal of the dichloromethane and pyridine solvents by evaporation, taken up in water (60 mL) and then extracted with ethyl acetate (3×50 mL). The organic extracts were then washed with water, brine, dried (MgSO$_4$) and evaporated to dryness. The product was then recrystallised to give 1-(4-cyanophenylsulphonyl)-4-(1-(4-pyridyl)piperidin-4-ylcarbonyl)piperazine as a white, hygroscopic solid m.p. 168–169° C.;

NMR: (CDCl$_3$) 1.83(m, 4H), 2.64(m, 1H), 2.88(td, 2H), 3.10(s, 4H), 3.68(bs, 4H), 3.88(dt, 2H), 6.64(dd, 2H); 7.86(s, 4H), 8.24(d, 2H); microanalysis found: C, 59.0; H, 5.7;

N, 15.2%; $C_{22}H_{25}N_5O_3S$ requires: C, 60.1; H, 5.7; N, 15.9%; MS: m/z 439 (MH)$^+$.

The starting material was prepared as follows:

1-(4-Pyridyl)isonipecotic acid (4.12 g, 20 mmol) was suspended in dry dichloromethane and treated with thionyl chloride (3 ml) dropwise with cooling to 0° C. The mixture was then stirred for one hour followed by the removal of the solvent and the excess thionyl chloride by evaporation. The resulting gum was then taken up in dichloromethane (80 ml) and added slowly, with cooling to a solution of t-butyl, 1-piperazinecarboxylate (3.72 g, 20 mmol) in dichloromethane (100 ml) and triethylamine (15 ml). The reaction mixture was then stirred for 2 hours and then the solvent was removed by evaporation. The residue was then taken up in ethyl acetate and recrystallised to give 4-(t-butoxy)-1-(4-pyridylpiperidin-4-ylcarbonyl)piperazine as a very pale yellow solid;

NMR: (CDCl$_3$) 1.45(s, 9H), 1.70–1.98(m, 4H), 2.35–2.52 (bs, 1H), 2.72(m, 1H), 2.92(td, 2H), 3.31–3.65(bs, 8H), 3.89(dt, 2H), 6.64(d, 2H), 8.22(d, 2H); MS: m/z 374 (MH)$^+$.

The 4-(t-butoxy)-1-(4-pyridylpiperidin-4-ylcarbonyl) piperazine (3.74 g) was then dissolved in dry dichloromethane (50 ml) and treated with trifluoroacetic acid (5.3 ml) and stirred under an argon atmosphere at room temperature for three hours. The dichloromethane solvent was then removed by evaporation to afford a brown oil which slowly solidified, This solid was then taken up in dichloromethane, filtered and washed with water, brine and then dried (MgSO$_4$). The resultant solution was then evaporated to dryness to yield a pale yellow oil which slowly crystallised to give 1-(4-pyridylpiperidin-4-ylcarbonyl) piperazine as a yellow solid;

NMR: 1.60(m, 4H), 2.66(m, 4H), 2.91 (td, 3H), 3.41 (dd, 4H), 3.92(dd, 2H), 6.78(d, 2H), 8.12(bd, 2H); MS: m/z 274 (MH)$^+$.

EXAMPLE 29

1-(1-(4-Pyridyl)piperidin-4ylcarbonyl)piperazine (0.722 g) was dissolved in dry dimethylformamide (22 mL) and treated with sodium hydride (0.19 g, 45–55% dispersion, 4 mmol) under argon atmosphere. The resultant mixture was then allowed to stir for 30 minutes before the addition of 4-bromobenzyl bromide (0.66 g). The reaction was then stirred at room temperature for 2 hours and then quenched by pouring into water, basifying with saturated aq.NaHCO$_3$ and then extracting with diethyl ether. The combined organic extracts were then washed with water, brine, dried (MgSO$_4$) and then evaporated to afford a crude, cream solid which was then recrystallised twice from ethyl acetate/isohexane to give 4-(4-bromophenylmethyl)-1-(1-(4-pyridyl)piperidin-4-ylcarbonyl)piperazine as a white solid; m.p. 148–149° C.; NMR: (CDCl$_3$) 1.84(m, 4H), 2.43(t, 4H), 2.72(m, 1H), 2.92(m, 2H), 3.49(s, 2H), 3.58(d, 4H), 3.90(dt, 2H), 6.66(d, 2H), 7.21(d, 2H); 7.46(d, 2H), 8.26(d, 2H); microanalysis found: C, 59.2; H, 6.1; N, 12.3%; $C_{21}H_{27}BrN_4O$ requires: C, 59.6; H, 6.14; N, 12.6%; MS: m/z 430 (MH)$^+$.

EXAMPLE 30

4-Chloro-2-methylpyrimidine (135 mg) was added to a solution of 1-(4-bromophenylsulphonyl)-4-(piperidin-4-ylcarbonyl)piperazine (415 mg) in THF (15 ml) containing triethylamine (0.2 ml). The mixture was heated at reflux for 16 hours. After cooling, the THF was evaporated. The residue was treated with H$_2$O (20 ml) and the aqueous extracted with EtOAc (3×20 ml). The combined organic phases were washed with saturated brine (1×20 ml) dried and evaporated to give an oil which was purified by chromatography on silica gel. Elution with CH$_2$Cl$_2$/MeOH/ 0.88NH$_3$ (96:3:1) gave an oil. Trituration with Et$_2$O (10 ml) gave, as a colourless solid, 1-(4-bromophenylsulphonyl) 4-(4-(1-(2-methylpyrimidyl)piperidin-4-ylcarbonyl) piperazine (152 mg), mp 200–202° C.;

NMR: 1.39–1.48 (m, 2H), 1.55–1.69 (m, 2H), 2.30 (s, 3H), 2.80–3.00 (m, 7H), 3.45–3.67 (m, 4H), 4.32 (m, 2H), 6.57 (d, 1H), 7.65 (d, 2H), 7.83 (d, 2H), 8.03 (d, 1H); EI-MS m/z 508 (M+H).

The starting 4-chloro-2-methylpyrimidine was prepared by the method described in Ger. Offen., DE 3905364 (Chem. Abs., 114, 81871).

EXAMPLE 31

4-Chloropyrimidine hydrochloride (3.5 g) was added to a stirred suspension of 1-benzyl-4-[1-piperidin-4-ylcarbonyl] piperazine (6.6 g), triethylamine (12.8 ml) and ethanol (120 ml). The mixture was heated under reflux for four hours then evaporated in vacuo to yield a treacle like substance. The residue was partitioned between ethyl acetate and water. The organic phase was washed with brine, dried (Na$_2$SO$_4$) and evaporated. The residue was absorbed onto alumina and purified using dry flash chromatography eluting with increasingly polar mixtures of methylene chloride and methanol (1:0 to 98:2). The material obtained was triturated with diethylether to give 1-(benzyl)-4-[1-(4-pyrimidinyl) piperidin-4-ylcarbonyl]piperazine (3.8 g, 45% yield); mp 107–108.5° C.;

NMR (CDCl$_3$): 1.80 (m, 4H), 2.45 (m, 4H), 2.80 (m, 1H), 3.00 (m, 2H), 3.60 (m, 6H), 4.40 (m, 2H), 6.50 (d, 1H), 7.35 (m, 5H), 8.15 (d, 1H), 8.55 (s, 1H); Microanalysis, found C, 68.7; H, 7.4; N 19.0%; $C_{21}H_{27}N_5O$ requires: C, 69.0; H, 7.45; N 19.2%.

EXAMPLE 32

A solution of $^4$-cyanobenzenesulphonyl chloride (363 mg) in methylene chloride (10 ml) was added to a stirred mixture of 1-[1-(4-pyrimidinyl) piperidin-4-ylcarbonyl]piperazine (412.5 mg) and triethylamine (0.28 ml) in methylene chloride (15 ml) and the resultant mixture was stirred at ambient temperature for 2 hours. The mixture was partitioned between methylene chloride and water. The organic phase was washed with water, dried (Na$_2$SO$_4$) and evaporated. The residue was purified by column chromatography using 0.5% methanol in methylene chloride. Recrystallisation from ethyl acetate/hexane gave, as a solid 1-(4-cyanobenzenesulphonyl)-4-[1-(4-pyrimidinyl)piperidin-4-ylcarbonyl]piperazine (280 mg), mp 180–181° C.;

NMR (CDCl$_3$): 1.7–1.8 (m, 4H), 2.7 (m, 1H), 2.9–3.0 (m, 2H), 3.0–3.1 (m, 4H), 3.6–3.8 (m, 4H), 4.4 (d, 2H), 6.5 (d, 1H), 7.9 (s, 4H), 8.2 (dd, 1H) and 8.6 (s, 1H).

The starting material was prepared as follows:

N-Benzylpiperazine (40.0 ml) was added in one portion to a solution of succinimido 1-t-butoxycarbonylpiperidine-4-carboxylate (75.0 g) in dry dichloromethane (1600 ml). The solution was stirred at ambient temperature under an atmosphere of argon for 17 hours. The solution was washed with water (500 ml) and saturated brine (250 ml). The organic layer was dried (Na$_2$SO$_4$) and evaporated. The residual oil was purified by chromatography on alumina, eluting with dichloromethane to give 1-benzyl-4-[(1-t-butoxycarbonyl-4-piperidyl)carbonyl]piperazine as an oil;

NMR (CDCl$_3$): 1.4–1.5 (9H, s), 1.6–1.85 (4H, m), 2.4–2.5 (4H, t), 2.5–2.65 (1H, m), 2.67–2.83 (2H, m), 3.45–3.7 (6H, m), 4.05–4.2 (2H, m) and 7.2–7.35 (5H, m); m/z 388 (M+H)$^+$.

A solution of 1-benzyl-4-[(1-t-butoxycarbonyl-4-piperidyl)carbonyl]piperazine (115.7 g) in dry dichloromethane (222 ml) was added dropwise over 45 minutes to trifluoroacetic acid (575 ml), maintaining the temperature below 25° C. under an atmosphere of argon. The solution was stirred at 23–25° C. for 1 hour. The solution was evaporated using a bath temperature of 30° C. The residual oil was poured, in portions, into saturated aqueous sodium carbonate solution (770 ml) while maintaining the temperature below 30° C. The aqueous mixture was extracted with dichloromethane (3×575 ml). The dichloromethane extracts were combined, dried ($Na_2SO_4$) and evaporated to give 1-benzyl-4-[(4-piperidyl)carbonyl]piperazine (56.2 g, 65% yield) as a white solid;

NMR ($CDCl_3$+$DMSOd_6$): 1.84–2.1 (4H, m), 2.33–2.5 (4H, m), 2.78–2.93 (1H, m), 2.93–3.12 (2H, m), 3.32–3.45 (2H, m), 3.45–3.65 (6H, m) and 7.2–7.37 (5H, m); m/z 288 (M+H).

Ammonium formate (1.88 g) was added to a mixture of 1-benzyl-4-[(1-[4-pyrimidinyl]-4-piperidyl)carbonyl]piperazine (2.73 g) and 10% palladium on carbon catalyst (0.55 g) in methanol (70 ml) under an atmosphere of argon. The mixture was stirred at reflux temperature for 1 hour. The cooled mixture was filtered through diatomaceous earth and the filtercake was well washed with methanol. The filtrate and washings were combined and evaporated. The residual oil was suspended in saturated aqueous sodium carbonate solution (30 ml) and the mixture was extracted with dichloromethane (4×100 ml). The dichloromethane extracts were combined, dried ($Na_2SO_4$) and evaporated to give 1-[(1-[4-pyrimidinyl]-4-piperidyl)carbonyl]piperazine (1.94 g, 94%) as an off-white solid;

NMR ($CDCl_3$): 1.75–1.95 (m, 4H), 2.7–3.15 (m, 8H), 3.4–3.7 (m, 4H), 4.3–4.47 (m, 2H), 6.45–6.55 (d, 1H), 8.12–8.23 (d, 1H) and 8.52–8.63 (s, 1H); m/z 276 (M+H).

EXAMPLE 33

Using an analogous procedure to that described in Example 32, 1-[1-(4-pyrimidinyl)piperidin-4-ylcarboxylpiperazine was reacted with the appropriate sulphonyl chloride to give the compounds listed below in Table VII

TABLE VII

| Compound No. | R | mpt (° C.) | NMR ($CDCl_3$) |
|---|---|---|---|
| 1 | 4-cyanophenyl | 180–181 | 1.7–1.8(m, 4H), 2.7(m, 1H), 2.9–3.0(m, 2H), 3.0–3.1(m, 4H), 3.6–3.8(m, 4H), 4.4 (d, 2H), 6.5(d, 1H), 7.9(s, 4H), 8.2(dd, 1H) and 8.6(s, 1H). |
| 2 | 2-chloro 4 cyano phenyl | 137–138 | 1.7–1.8(m, 4H), 2.7(m, 1H), 2.9–3.0(m, 2H), 3.2–3.5(m, 4H), 3.6–3.8(m, 4H), 4.4 (d, 2H), 6.5(d, 1H), 7.7(dd, 1H), 7.9(s, 1H), 8.2(dd, 1H), 8.2(d, 1H) and 8.6(s, 1H). |
| 3 | 3,4-dichloro phenyl | 189–190 | 1.7–1.8(m, 4H), 2.7(m, 1H), 2.9–3.0(m, 2H), 3.0–3.1(m, 4H), 3.6–3.8(m, 4H), 4.4 (d, 2H), 6.5(d, 1H), 7.5–7.7(m, 2H), 7.9(s 1H), 8.2(dd, 1H) and 8.6(s, 1H). |
| 4 | 4-methoxy phenyl | 205–206 | 1.7–1.8(m, 4H), 2.7(m, 1H), 2.9–3.0(m, 2H), 3.0–3.1(m, 4H), 3.6–3.8(m, 4H), 3.9(s, 3H), 4.4(d, 2H), 6.5(d, 1H), 7.0(d, 2H), 7.7 (d, 2H), 8.2(dd, 1H) and 8.6(s, 1H). |
| 5 | 4-chlorophenyl | 196–197 | 1.7–1.8(m, 4H), 2.7(m, 1H), 2.9–3.0(m, 6H), 3.6–3.8(m, 4H), 4.4(d, 2H), 6.5(d, 1H), 7.5(d, 2H), 7.7(d, 2H), 8.2(d, 1H) and 8.6(s, 1H). |
| 6 | 2-cyanophenyl | sublimed 100 | 1.7–1.8(m, 4H), 2.75(m, 1H), 3.0(m, 2H), 3.1–3.5(m, 4H), 3.6–3.8(m, 4H), 4.4(d, 2H), 6.5(d, 1H), 7.75(m, 2H), 7.9(dd, 1H), 8.15(dd, 1H), 8.2(d, 1H) and 8.55(s, 1H). |
| 7 | 2,4-difluoro phenyl | decomp. 170–175 | 1.7–1.8(m, 4H), 2.75(m, 1H), 3.0(m, 2H), 3.25(m, 4H), 3.6–3.8(m, 4H), 4.4(d, 2H), 6.5(d, 1H), 7.0(m, 2H), 7.8(m, 1H), 8.15 (d, 1H) and 8.55(s, 1H). |
| 8 | 4-(n-butoxy) phenyl | 115–117 | 0.95–1.05(t, 3H), 1.4–1.65(m, 2H), 1.65–1.9 (m, 6H), 2.6–2.8(m, 1H), 2.85–3.1(m, 6H), 3.5–3.8(m, 4H), 3.95–4.05(t, 2H), 4.3–4.45 (m, 2H), 6.45–6.5(dd, 1H), 6.95–7.05(d, 2H), 7.6–7.7(d, 2H), 8.15–8.2(d, 1H), 8.55–8.6(s, 1H). |
| 9 | 4-t-butylphenyl | 220–221 | 1.3–1.4(s, 9H), 1.65–1.9(m, 4H), 2.6–2.8 (m, 1H), 2.9–3.1(m, 6H), 3.55–3.8(m, 4H), 4.3–4.45(m, 2H), 6.45–6.5(dd, 1H), 7.5–7.6 |

TABLE VII-continued

| Compound No. | R | mpt (° C.) | NMR (CDCl₃) |
|---|---|---|---|
| | | | (d, 2H), 7.6–7.7(d, 2H), 8.15–8.2(d, 1H), 8.55–8.6(s, 1H). |
| 10 | 4-isopropyl phenyl | 170–171 | 1.2–1.35(d, 6H), 1.65–1.9(m, 4H), 2.6–2.8 (m, 1H), 2.85–3.15(m, 6H), 3.55–3.8(m, 4H), 4.3–4.45(m, 2H), 6.45–6.5(dd, 1H), 7.35–7.45(d, 2H), 7.6–7.7(d, 2H), 8.15–8.2 (d, 1H), 8.55–8.6(s, 1H). |
| 11 | 2-thiophenyl | 164–165 | 1.76(m, 4H), 2.72(m, 1H), 3.00 (m, 6H), 3.69(bs, 4H), 4.38(dt, 2H), 6.48 (d, 1H), 7.17(dd, 1H), 7.55(dd, 1H), 7.66 (dd, 1H), 8.17(d, 1H), 8.57(s, 1H) |
| 12 | 5-chloro-(2-thiophenyl) | 159–160 | 1.75(m, 4H), 2.72(m, 1H), 3.02(m, 6H), 3.68(bs, 4H), 4.41(dt, 2H), 6.51(dd, 1H), 7.02(d, 1H), 7.33(d, 1H), 8.16(d, 1H), 8.58 (s, 1H) |
| 13 | 2,5-dichloro-(3-thiophenyl) | 148–149 | 1.80(m, 4H), 2.74(m, 1H), 3.00(m, 2H), 3.22(bs, 4H), 3.68(bs, 4H), 4.39(dt, 2H), 6.49(dd, 1H), 7.02(s, 1H), 8.18(d, 1H), 8.58(s, 1H) |
| 14 | 5-bromo-(2-thiophenyl) | 163–164 | 1.77(m, 4H), 2.72(m, 1H), 3.00(m, 2H), 3.20(bs, 4H), 3.72(bs, 4H), 4.40(dt, 2H), 6.50(dd, 1H), 7.15(d, 1H), 7.32(d, 1H), 8.18(d, 1H), 8.57(s, 1H) |
| 15 | 4,5-dibromo-(2-thiophenyl) | 221–222 | 1.78(m, 4H), 2.72(m, 1H), 3.00(m, 2H), 3.12(bs, 4H), 3.72(bs, 4H), 4.39(dt, 2H), 6.50(dd, 1H), 7.34(s, 1H), 8.18(d, 1H), 8.58(s, 1H) |
| 16 | 4,5-dichloro-(2-thiophenyl) | 215–216 | (CDCl₃)δ 1.78(m, 4H), 2.72(m, 1H), 2.98 (m, 2H), 3.12(bs, 4H), 3.72(bs, 4H), 4.40 (dt, 2H), 6.48(dd, 1H), 7.32(s, 1H), 8.18(d, 1H), 8.58(s, 1H) |
| 17 | | 215–216 | (CDCl₃)δ 1.77(m, 4H), 2.77(m, 1H), 3.02 (m, 2H), 3.13(bs, 2H), 3.33(bs, 2H), 3.65 (bs, 4H), 3.77(s, 3H), 4.39(dt, 2H), 6.52 (dd, 1H), 7.47(d, 1H), 7.53(d, 1H), 8.18(d, 1H), 8.58(s, 1H) |

TABLE VII-continued

| Compound No. | R | mpt (° C.) | NMR (CDCl$_3$) |
|---|---|---|---|
| 18 | (5-methyl-thien-2-yl)-pyridine | 108–109 | (CDCl$_3$)δ 1.75(m, 4H), 2.72(m, 1H), 2.98 (m, 2H), 3.15(bs, 4H), 3.70(bs, 4H), 4.37 (dt, 2H), 6.48(dd, 1H), 7.29(m, 1H), 7.53 (m, 2H), 7.78(m, 2H), 8.17(d, 1H), 8.56(s, 1H), 8.62(dd, 1H) |
| 19 | 3,5-dimethylisoxazol-4-yl | 113–114 | (CDCl$_3$)δ 1.79(m, 4H), 2.37(s, 3H), 2.62 (s, 3H), 2.74(m, 1H), 2.98(m, 2H), 3.14 (bs, 4H), 3.67(bs, 4H), 4.39(dt, 2H), 6.50 (dd, 1H), 8.17(d, 1H), 8.57(s, 1H) |
| 20 | cyclohexylmethyl | 207–208 | (CDCl$_3$)δ 1.26(m, 4H), 1.42–1.66(m, 2H), 1.66–2.01(m, 6H), 2.12(d, 2H), 2.78(m, 1H), 2.84–3.12(m, 3H), 3.37(bs, 4H), 3.64 (bs, 4H), 4.42(dt, 2H), 6.54(dd, 1H), 8.20 (d, 1H), 8.59(s, 1H). |
| 21 | 3,5-dimethyl 4-fluorophenyl | 180–181 | 1.7–1.8(m, 4H), 2.3(s, 6H), 2.7(m, 1H), 2.9–3.1(m, 6H), 3.6–3.8(m, 4H), 4.4(m, 2H), 6.5(dd, 1H), 7.4(d, 2H), 8.2(d, 1H), and 8.6(s, 1H). |
| 22 | 2,5-dibromo 3,6-difluoro phenyl | 148–149 | 1.7–1.8(m, 4H), 2.7(m, 1H), 3.0(m, 2H), 3.3–3.5(m, 4H), 3.6–3.8(m, 4H), 4.4(d, 2H), 6.5(d, 1H), 7.6(m, 1H), 8.2(d, 1H) and 8.6(s, 1H). |
| 23 | 4-iodophenyl | 194–195 | 1.7–1.8(m, 4H), 2.7(m, 1H), 2.9–3.1(m, 6H), 3.6–3.8(m, 4H), 4.4(d, 2H), 6.5(d, 1H), 7.4(d, 2H), 7.9(d, 2H), 8.2(d, 1H) and 8.6(s, 1H). |
| 24 | 4-acetylamino phenyl | 273–275 | 1.7–1.8(m, 4H), 2.2(s, 3H), 2.7(m, 1H), 2.9–3.1(m, 6H), 3.6–3.8(m, 4H), 4.4(d, 2H), 6.5(d, 1H), 7.5(s, 1H), 7.7(s, 4H), 8.2 (d, 1H) and 8.6(s, 1H). |
| 25 | phenyl | 159–160 | 1.7–1.8(m, 4H), 2.7(m, 1H), 2.9–3.1(m, 6H), 3.6–3.8(m, 4H), 4.4(d, 2H), 6.5(d, 1H), 7.6(m, 3H), 7.8(dd, 2H), 8.2(d, 1H) and 8.6(s, 1H). |
| 26 | 4-ethylphenyl | 171–174 | 1.2–1.35(t, 3H), 1.65–1.9(m, 4H), 2.6–2.8 (m, 3H), 2.85–3.1(m, 6H), 3.5–3.8(m, 4H), 4.3–4.45(m, 2H), 6.45–6.5(d, 1H), 7.3–7.4 (d, 2H), 7.6–7.7(d, 2H), 8.15–8.2(d, 1H) and 8.55–8.6(s, 1H). |
| 27 | 4-(n-propyl) phenyl | 138–140 | 0.87–1.03(t, 3H), 1.6–1.9(m, 6H), 2.55–2.8 (m, 3H), 2.85–3.15(m, 6H), 3.55–3.8(m, 4H), 4.3–4.5(m, 2H), 6.45–6.55(d, 1H), 7.3–7.4(d, 2H), 7.6–7.7(d, 2H), 8.15–8.25(d, 1H) and 8.55–8.6(s, 1H). |
| 28 | 2,2,2-trifluoroethyl CH$_2$CF$_3$ | foam | $^1$H-NMR(200/250mhz)(CDCl$_3$): δ: 1.73–1.83 (m, 4H), 2.72–2.83(m, 1H), 2.96–3.06(m, 2H), 3.35–3.43(m, 4H), 3.60–3.78(m, 6H), 4.35–4.46(m, 2H), 6.52(dd, 1H), 8.20(d, 1H), 8.60 (s, 1H). |
| 29 | n-butyl CH$_2$CH$_2$CH$_2$CH$_3$ | foam | $^1$H-NMR(200/250mhz)(CDCl$_3$): δ: 0.97 (t, 3H), 1.40–1.54(m, 2H), 1.76–1.86(m, 6H), 2.72–2.85(m, 1H), 2.90–3.08(m, 4H), 3.23–3.37(m, 4H), 3.60–3.78(m, 4H), 4.35–4.47 (m, 2H), 6.52(dd, 1H), 8.20(d, 1H), 8.60 (s, 1H). |

TABLE VII-continued

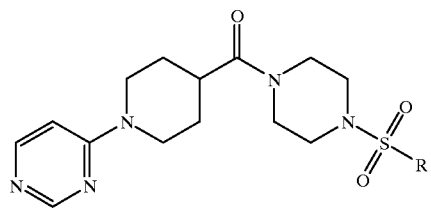

| Compound No. | R | mpt (° C.) | NMR (CDCl₃) |
|---|---|---|---|
| 30 | i-propyl —CHMe₂ | foam | ¹H-NMR(200/250MHz)(DMSO-D6): δ 1.25 (d, 6H), 1.40–1.60(m, 2H), 1.65–1.80(m, 2H), 2.90–3.10(m, 3H), 3.15–3.45(m, 5H), 3.45–3.70(m, 4H), 4.30–4.45(m, 2H), 6.82(dd, 1H), 8.15(d, 1H), 8.48(s, 1H) |
| 31 | methyl | 177–179 | 1.7–1.8(m, 4H), 2.75(m, 1H), 2.8(s, 3H), 3.0(m, 2H), 3.2–3.6(m, 4H), 3.6–3.8(m, 4H), 4.4(d, 2H), 6.5(d, 1H), 8.2(d, 1H) and 8.6(s, 1H). |
| 32 | 4-tolyl | 191–192 | 1.7–1.8(m, 4H), 2.4(s, 3H), 2.7(m, 1H), 2.9–3.1(m, 6H), 3.6–3.8(m, 4H), 4.4(d, 2H), 6.5(d, 1H), 7.3(d, 2H), 7.6(d, 2H), 8.2(d, 1H) and 8.6(s, 1H). |
| 33 | 2,5-dibromo phenyl | 152–153 | 1.7–1.8(m, 4H), 2.75(m, 1H), 3.0(m, 2H), 3.2–3.5(m, 4H), 3.6–3.8(m, 4H), 4.4(d, 2H), 6.5(d, 1H), 7.5(dd, 1H), 7.6(d, 1H), 8.2(d, 1H), 8.25(d, 1H) and 8.6(s, 1H). |
| 34 | 3,5-bis-trifluoromethyl phenyl | 227–228 | 1.7–1.8(m, 4H), 2.7(m, 1H), 3.0(m, 2H), 3.2(m, 4H), 3.6–3.8(m, 4H), 4.4(d, 2H), 6.5(d, 1H), 8.15(d, 1H), 8.2(m, 3H) and 8.6 (s, 1H). |
| 35 | 4-nitrophenyl | 219–220 | 1.7–1.8(m, 4H), 2.7(m, 1H), 2.9–3.0(m, 2H), 3.1–3.2(m, 4H), 3.6–3.8(m, 4H), 4.4(d, 2H), 6.5(d, 1H), 8.0(d, 2H), 8.2(d, 1H), 8.4 (d, 2H) and 8.6(s, 1H). |
| 36 | 4-chloro 3-nitrophenyl | 246–248 | 1.7–1.8(m, 4H), 2.7(m, 1H), 2.9–3.0(m, 2H), 3.1–3.2(m, 4H), 3.6–3.8(m, 4H), 4.4(d, 2H), 6.5(d, 1H), 7.8(d, 1H), 7.9(d, 1H), 8.15 (d, 1H), 8.2(d, 1H) and 8.6(s, 1H). |
| 37 | 2-methoxy carbonylphenyl | 133–134 | 1.7–1.8(m, 4H), 2.75(m, 1H), 3.0(m, 2H), 3.2–3.3(m, 4H), 3.6–3.8(m, 4H), 3.95(s, 3H), 4.4(d, 2H), 6.5(d, 1H), 7.5(dd, 1H), 7.6(m, 2H), 7.8(dd, 1H), 8.2(d, 1H) and 8.6 (s, 1H). |
| 38 | 3,4-dibromo phenyl | 192–194 | 1.65–1.9(m, 4H), 2.6–2.8(m, 1H), 2.9–3.15 (m, 6H), 3.55–3.85(m, 4H), 4.3–4.48(m, 2H), 6.45–6.55(dd, 1H), 7.48–7.57(dd, 1H), 7.8–7.85(d, 1H), 7.95–8.0(d, 1H), 8.15–8.25 (d, 1H) and 8.55–8.6(s, 1H). |
| 39 | 2,4,5-trichloro phenyl | 157–159 | 1.65–1.9(m, 4H), 2.65–2.85(m, 1H), 2.9–3.1 (m, 2H), 3.2–3.5(m, 4H), 3.5–3.8(m, 4H), 4.3–4.5(m, 2H), 6.45–6.55(d, 1H), 7.65(s, 1H), 8.15(s, 1H), 8.15–8.2(d, 1H) and 8.55–8.6(s, 1H). |
| 40 | 2,4,6-trimethyl phenyl | 141–142 | 1.7–1.8(m, 4H), 2.3(s, 3H), 2.6(s, 6H), 2.7 (m, 1H), 2.9–3.0(m, 2H), 3.1–3.3(m, 4H), 3.6–3.7(m, 4H), 4.4(d, 2H), 6.5(d, 1H), 7.0 (s, 2H), 8.2(d, 1H) and 8.6(s, 1H). |
| 41 | 3,5-dichloro phenyl | 186–187 | 1.7–1.8(m, 4H), 2.7(m, 1H), 2.9–3.0(m, 2H), 3.0–3.1(m, 4H), 3.6–3.8(m, 4H), 4.4 (d, 2H), 6.5(d, 1H), 7.6(s 3H), 8.2(dd, 1H) and 8.6(s, 1H). |
| 42 | 2-chloro 4 fluorophenyl | 135–137 | 1.7–1.9(m, 4H), 2.7(m, 1H), 2.9–3.1(m, 2H), 3.2–3.4(m, 4H), 3.6–3.8(m, 4H), 4.4 (d, 2H), 6.5(d, 1H), 7.1(m, 1H), 7.3(m, 1H), 8.1(m, 1H), 8.2(d, 1H) and 8.6(s, 1H). |
| 43 | 4-trifluoro methoxyphenyl | 178–179 | 1.7–1.8(m, 4H), 2.7(m, 1H), 2.9–3.0(m, 2H), 3.0–3.1(m, 4H), 3.6–3.8(m, 4H), 4.4 (d, 2H), 6.5(d, 1H), 7.4(d, 2H), 7.8(d, 2H), 8.2(dd, 1H) and 8.6(s, 1H). |

TABLE VII-continued

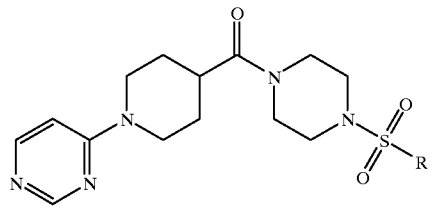

| Compound No. | R | mpt (° C.) | NMR (CDCl₃) |
|---|---|---|---|
| 44 | 2-chloro 4 trifluoromethyl phenyl | 152–153 | 1.7–1.9(m, 4H), 2.7–2.8(m, 1H), 2.9–3.1(m, 2H), 3.2–3.5(m, 4H), 3.6–3.8(m, 4H), 4.4 (d, 2H), 6.5(d, 1H), 7.7(dd, 1H), 7.8(s, 1H), 8.2(m, 2H) and 8.6(s, 1H). |

EXAMPLE 34

A solution of hydrogen bromide in glacial acetic acid (5 ml) was added 1-(6-chloronaphth-2-ylsulphonyl)-4-(1-(benzyloxycarbonyl)piperidin-4-ylcarbonyl)-3-(methoxycarbonyl)piperazine (512 mg). After stirring for 20 minutes. at ambient temperature, ether (100 ml) was added and the mixture stirred vigourously. The ether was decanted and the resulting white solid was washed with further portions of ether (5×100 ml) and then dried under high vacuum. Methanol (20 ml) was added and then 4-chloropyrimidine (189 mg) and triethylamine (1.39 ml) were added. The mixture was heated at reflux for 18 hours. After dilution with water (100 ml) the reaction mixture was extracted with ethyl acetate (3×25 ml). The combined extracts were washed with water (25 ml) and brine (25 ml), dried (MgSO₄) and evaporated to give a yellow oil which was purified by chromatography on silica gel [Mega Bodn Elut column] using a gradient of 0% to 4% MeOH in CH₂Cl₂ as eluent to give 1-(6-chloronaphth-2-ylsulphonyl)-3-methoxycarbonyl-4-(4-pyrimidinyl piperidin-1-ylcarbonyl)piperazine (2) as a white solid. (362 mg);
NMR (CDCl3): 1.6–2.0 (m, 4H), 2.4–2.6 (m, 2H), 2.75–2.85 (m, 1H), 2.9–3.1 (m, 2H), 3.6–3.9 (m, 6H), 4.25–4.45 (m, 3H), 5.3–5.4 (m, 1H), 6.5 (d, 1H), 7.8 (dd, 1H), 7.75 (dd, 1H), 7.9–8.0 (m, 3H), 8.2 (d, 1H), 8.35 (s, 1H), 8.6 (s, 1H): MS M/Z 558 (M+H).

The starting materials were prepared as follows:
The benzyloxycarbonyl protected isonipecotic acid (622 mg) was dissolved in dichloromethane (20 ml). Oxalyl chloride (0.429 ml) and one drop of DMF was added. The mixture was stirred at ambient temperature for 2 hours and then evaporated. The residue was redissolved in dichloromethane (10 ml) and added dropwise with stirring and ice cooling to a solution the amine (4) (930 mg) and triethylamine (0.7 ml) in dichloromethane (10 ml). After stirring at ambient temperature for 2 hours, the reaction mixture was diluted with ethyl acetate (150 ml), washed with 2M hydrochloric acid (50 ml) saturated aqueous sodium bicarbonate (50 ml), water (2×50 ml) and brine (25 ml), dried (MgSO₄) and evaporated to give a yellow oil. This was further purified by flash column chromatography on silica gel using a gradient of ETOAc/Hexane (50/50–80/20) as eluent to give 1-(6-chloronaphth-2-ylsulphonyl)-4-(1-(benzyloxycarbonyl)piperidin-4-ylcarbonyl)-3-(methoxycarbonyl)piperizine (1.21 g);
NMR (CDCl3): 1.4–1.9 (m, 4H), 2.3–2.7 (m, 3H), 2.7–3.0 (m, 2H), 3.5–3.9 (m, 6H), 4.05–4.25 (m, 2H), 4.3–4.4 (m, 1H), 5.1 (s, 2H), 5.25–5.35 (m, 1H), 7.2–7.4 (m, 5H), 7.6 (dd, 1H), 7.75 (dd, 1H), 7.75–8.0 (m, 3H), 8.3 (s, 1H); MS: 614 (M+H).

EXAMPLE 35

4-(1-(4-Pyrimidinyl)piperazin-4ylcarbonyl)piperidine (412 mg; 1.5 mmol) was dissolved in CH₂Cl₂ (16 ml), cooled in an ice bath, stirred and treated dropwise with a mixture of 4-Chlorobenzenesulfonyl chloride (338 mg; 1.6 mmol) and Et₃N (0.3 ml; 2 mmol) in CH₂Cl₂ (16 ml). The reaction mixture was allowed to reach room temperature and stirred thus for 18 h before treating with saturated NaHCO₃ (aq) This mixture was then extacted twice with CH₂Cl₂. The combined organic extracts were washed twice each with water and brine, dried over MgSO₄, filtered and evaporated under reduced pressure to a yellow solid. The solid thus obtained was chromatographed through a 10 g silica "bond elut" prepacked column, eluting with 1% methanol, 1% ammonimum hydroxide and 98% CH₂Cl₂ to obtain 1-(4-chlorophenylsulphonyl)-4-(1-(4-pyrimidinyl)piperazin-4-ylcarbonyl)piperidine (178 mg; 26% yield based on the amine ), a white solid, m.p. 125–128° C.;
NMR (CDCl₃): 1.75–1.89ppm (m, 2H), 1.88–2.02 (m, 2H), 2.45–2.58 (m, 3H), 3.48–3.81 (m, 10H), 6.51 (dd, 1H), 7.52 (dd, 2H), 7.73 (dd, 2H), 8.25 (d, 1H), 8.64 (d, 1H).

EXAMPLE 36

4-(1-(4-Pyrimidinyl)piperazin-4-ylcarbonyl)piperidine (385 mg; 1.4 mmol) in CH₂Cl₂ (20 ml) was stirred at room temperature as a solid suspension and treated dropwise with 4-Bromobenzenesulfonyl chloride (385 mg; 1.5 mmol) and Et₃N (0.4 ml; 3 mmol) in CH₂Cl₂ (15 ml). The resulting clear yellow solution was stirred at the same temperature for a further 20 h then treated with saturated NaHCO₃₍aq₎ (40 ml). The mixture was extracted twice with CH₂Cl₂ and the combined organic extracts washed twice each with water and brine then dried over anhydrous MgSO₄, filtered and evaporated under reduced pressure to a yellow solid. The solid was chromatographed through a 10 g silica bond elut prepacked column, eluting with 1% methanol, 1% ammonium hydroxide and 98% CH₂Cl₂ to give 1-(4-bromophenylsulphonyl)-4-(1-(4-pyrimidinyl)piperazin-4-ylcarbonyl)piperidine (209 mg; 30% yield based on the amine), a white solid, m.p. 171–174° C.;
NMR: (CDCl₃) 1.74–1.88ppm (m, 2H), 1.86–2.03 (m, 2H), 2.45–2.58 (m, 3H), 3.49–3.82 (m, 10H), 6.49 (dd, 1H), 7.60–7.71 (m, 4H), 8.25 (d, 1H), 8.62 (d, 1H).

The starting material was prepared as follows:

1-(t-Butoxycarbonyl)4-(1-(4-pyrimidinyl)piperazin-4-ylcarbonyl)piperidine (5.23 g; 14 mmol) was dissolved in $CH_2Cl_2$ (50 ml) and treated at room temperature with trifluoroacetic acid (30 ml; 392 mmol). The resulting pale yellow solution was stirred at the same temperature for 18 h. After this period the reaction mixture was evaporated under reduced pressure to a brown oil which was subsequently azeotroped with toluene. The resulting oil was basified with 40% w/v NaOH (aq) then taken up in $CH_2Cl_2$ and filtered through celite. The filtrate was washed twice with brine, dried over anhydrous $MgSO_4$, filtered and evaporated under reduced pressure to obtain the amine, a brown foam, 1.545 g (40% yield based on the boc derivative);
NMR ($CDCl_3$) 1.67–1.80 ppm (m, 4H), 2.64–2.79 (m, 3H), 3.15–3.25 (m, 2H), 3.55–3.79 (m, 8H), 6.51 (dd, 1H), 8.26 (d, 1H), 8.63 (d, 1H).

A further sample of the amine was obtained by washing the celite again with 10% methanol, 1% ammonium hydroxide and 89% $CH_2Cl_2$. This too was washed with brine (3 times), dried over anhydrous $MgSO_4$, filtered and evaporated down to a complex white foam. The foam was chromatographed through 60um silica gel, eluting with 10% methanol, 1% ammonium hydroxide and 89% $CH_2Cl_2$ to obtain a further 676 mg (18% based on the boc derivative) of the amine.

4-Pyrimidyl piperazine (2.473 g; 14 mmol) was dissolved in DMF (35 ml) and treated at room temperature with 1-(1-(t-butoxycarbonyl)piperidin-4-ylcarbonyloxy)2,5-dioxopyrrolidine (4.9 g; 15 mmol). The resulting clear solution was stirred at the same temperature for 65 h to give a pale yellow solid suspension. The reaction mixture was drowned out in water (350 ml) and extracted four times with $CH_2Cl_2$. The combined organic extracts were then washed twice each with water and brine, dried over anhydrous $MgSO_4$, filtered and evaporated under reduced pressure to obtain a crude oil. The oil was dried on a high vacuum pump to yield a white solid which was recrystallised with ethyl acetate/i-hexane to afford 1-(!-butoxycarbonyl)-4-(1-(4-pyrimidinyl)piperazin-4-ylcarbonyl)piperidine white crystals (5.05 g; 90% yield based on 4-pryimidyl piperazine), m.p. 159–163° C.;
NMR: ($CDCl_3$) 1.44ppm (s, 9H), 1.54–1.85 (m, 4H), 2.59–2.70 (m, 1H), 2.74–2.86 (m, 2H), 3.56–3.82 (m, 8H), 4.11–4.22 (m, 2H), 6.52 (dd, 1H), 8.25 (d, 1H), 8.63 (d, 1H).

1-(Benzyl)-4-(4-chloropyrimidin-6-yl)piperazine (58.0 g; 0.20 mol) was dissolved, with some heating, in methanol (700 ml), treated with 10% Pd on activated carbon (11.6 g) and agitated and hydrogenated at s.t.p. for 8 h. After this period the catalyst was removed by filtering through celite. The filtrate thus obtained was then evaporated under reduced pressure to a yellow-brown viscous gum which was chromatographed through 60 μm silica gel, eluting with 5% methanol, 1% ammonium hydroxide and 94% $CH_2Cl_2$ to obtain as white solid, 25 g (76% yield based on prehydrogenation substrate) of 4-(4-pyrimidinyl)piperazine;
NMR: (t, 4H), 3.50 (t, 4H), 6.75 (dd, 1H), 8.14 (d, 1H), 8.45 (d, 1H).

A mixture of 4,6-dchloropyrimidine (29.5 g; 0.2 mol), N-bnzylpiperazine (44.0 g; 0.25 mol) and DIPEA (44 ml; 0.25mol) was suspended in p-xylene (400 ml) and heated at 138° C. under reflux. Once reflux temperature had been reached, the reaction mixture took the appearance of a black solution. After heating at this temperature for 18 h the reaction mixture was allowed to cool to room temperature and filtered. The filtrate was evaporated using high vacuum pump apparatus to obtain 1-(benzyl)-4-(4-chloropyrimidin-6-yl)piperazine a brown solid, 60.5 g (105% based on 4,6-dichloropyrimidine);
NMR: ($CDCl_3$) 2.51 ppm (t, 4H), 3.56 (s, 2H), 3.65 (t, 4H), 6.47 (s, 1H), 7.27–7.37 (m, 5H), 8.36 (s, 1H).

EXAMPLE 37

1-(4-Bromophenylsulphonyl)-4-(1-(t-butoxycarbonyl) piperidin-4-ylcarbonyl) 1,4-diazepine was dissolved in dichloromethane (15 ml). Trifluoroacetic acid (3 ml) was added, and the reaction stirred at room temperature for 1 hour. The solvent was removed in vacuo to give the crude trifluoroacetic acid salt of the deprotected piperidine. The crude salt was dissolved in ethanol (15 ml). Triethylamine (1 ml) and 4-chloropyrimidine hydrochloride (90 mg) were added. The reaction was then refluxed for 2 hrs. Solvent removed in vacuo. The residue was partitioned between dichloromethane (50 ml) and aqueous sodium bicarbonate solution (50 ml). Product extracted with dichloromethane (2×50 ml), dried ($MgSO_4$) and solvent removed in vacuo. The product was purified on a bond elute column (10 g, Si) eluting with dichloromethane and then with [1% methanol, 1% ammonia, 98% dichloromethane] to give 1-(4-bromophenylsulphonyl)-4-(1-(4-pyrimidinyl)piperidin-4-ylcarbonyl) 1,4-diazepine as a foam (152 mg);
NMR (250 mhz) 1.40–1.95 (m, 6H), 2.85–3.1 (m, 3H), 3.25–3.80 (m, 8H), 4.35–4.55 (m, 2H), 6.90 (d, 1H), 7.78 (d, 1H), 7.82 (d, 1H), 7.85–7.95 (m, 2H), 8.20 (d, 1H), 8.53 (s, 1H).

The starting material was prepared as follows:
1-(1-(t-Butoxycarbonyl)piperidin-4-ylcarbonyloxy)2,5-dioxopyrrolidine (450 mg) and 1-(4-bromophenylsulphonyl) 1,4-diazepine (440 mg) were refluxed together in dichloromethane (25 ml) for 3 hrs. The reaction was stood at room temperature for 60 hrs. The solvent was removed in vacuo and the residue was partitioned between ethyl acetate (50 ml) and dilute citric acid (50 ml). The organic layer was washed with brine, dried ($MgSO_4$) and the solvent removed in vacuo. The product was purified on a bond elute column (Si, 10 g) eluting with ethyl acetate/hexane (40:60) raising polarity gradually to (60:40). The product 1-(4-bromophenylsulphonyl)-4-(1-(t-butoxycarbonyl)piperidin-4-ylcarbonyl)1,4-diazepine was obtained as a foam (620 mg);
NMR (250 MHz) 1.30–1.85 (m, 6H), 1.40 (3, 9H), 2.63–2.87 (m, 3H), 3.20–3.68 (m, 8H), 3.85–3.98 (m, 2H), 7.67–7.77 (m, 2H), 7.77–7.87 (m, 2H).

4-Bromobenzenesulphonyl chloride (1.50 g) in dichloromethane (50 ml) was added slowly to a solution of homopiperazine (3.0 g) in dichloromethane (100 ml). The reaction was stirred at room temperature for 18 hrs. The reaction mixture was washed with water (40 ml) and brine (50 ml), dried ($MgSO_4$) and solvent removed in vacuo. The product was recrystallised from dichloromethane/hexane to give 1-(4-bromophenylsulphonyl) 1,4-diazepine a white solid (650 mg), mp 95–97° C.;
NMR (250 MHz) 1.57–1.75 (m, 2H), 2.67–2.79 (m, 4H), 3.15–3.30 (m, 4H), 7.73 (d, 2H), 7.82 (d, 2H).

EXAMPLE 38

The lithium salt of 1-(4-pyrimidinyl)piperidine-4-carboxylic acid (426 mg), thionyl chloride (15 ml) and DMF (5 drops) were refluxed together for 1.5 hrs. The thionyl chloride was removed in vacuo. Toluene (20 ml) was added, and removed in vacuo to give the crude acid chloride. A solution of the 1-(4-bromophenylsulphonyl)piperazine (610 mg) and triethylamine (2 ml) in dichloromethane (10 ml) was added to a solution of the crude acid chloride in dichloromethane (5 ml) cooled in an ice bath. After addition of the reagents the ice bath was removed and the reaction was stirred at room temperature for 1 hr. Water (30 ml) was added. The mixture was washed with water (2×30 ml), dried ($MgSO_4$) and the solvent removed. The reaction mixture was purified on a bond elute column (Si, 10 g), eluting initially with dichloromethane and increasing polarity to 3% methanol, 1% ammonia, 96% dichloromethane. This gave 1-(4-bromophenylsulphonyl)-4-(1-(5-chloropyrimidin-4-yl)piperidin-4-ylcarbonyl)piperazine (280 mg) and the monochloro derivative (110 mg) as a foam, mp 165–167° C.; NMR (250 MHz) 1.45–1.73 (m, 4H), 2.83–3.10 (m, 7H), 3.45–3.70 (m, 4H), 4.22–4.35 (m, 2H), 7.67 (d, 2H), 7.97 (d, 2H), 8.34 (s, 1H), 8.50 (s, 1H).

The starting material was prepared as follows:

A solution of 1-(4-pyrimindinyl)-4-(ethoxycarbonyl)piperidine (1.52 g) and lithium hydroxide monohydrate (300 mg) in ethanol (20 ml) and water (20 ml) was refluxed for 1.5 hrs. The solvents were removed in vacuo to give the crude lithium salt of 1-(4-pyrimidinyl)piperidine-4-carboxylic acid (1.46 g) which was used without purification. A solution of 4,6-dichloropyrimidine (5.22 g), ethyl isonipecotate (5.50 g) and triethylamine (7 ml) in ethanol (60 ml) was stirred at room temperature for 2 hrs. The solvent was removed in vacuo and the crude mixture partitioned between ethyl acetate (100 ml) and water (50 ml), washed with brine, dried (MgSO$_4$) and solvent removed to give 1-(6-chloropyrimidin-4-yl)-4-(ethoxycarbonyl)piperidine.

Ammonium formate (10 g) and 30%Pd/C (600 mg) was added to a solution of the crude mono-chloro pyrimidylpiperazine in ethanol (70 ml). The reaction was stirred at room temperature for 18 hrs and then filtered through celite and the solvent removed in vacuo. Crude product was partitioned between dichloromethane/sodium bicarbonate solution and extracted with dichloromethane (3×50 ml). Combined extracts dried (MgSO$_4$) and solvent removed. he product was purified by flash column chromatography (3% methanol/ethyl acetate) to give 1-(4-pyrimidinyl)-4-(ethoxycarbonyl)piperidine an oil (5.44 g);
NMR (250 MHz) 1.2 (t, 3H), 1.40–1.60 (m, 2H), 2.10–2.25 (m, 1H), 3.0–3.13 (m, 2H), 4.07 (q, 2H), 4.20–4.35 (m, 2H), 6.82 (d, 1H), 8.13 (d, 1H), 8.45 (s, 1H).

EXAMPLE 39

4-(1-(4-Bromophenylsulphonyl)piperazin-4-ylcarbonyl)piperidine (170 mg) and 4-chloro pyrimidine 0.2 HCl in absolute alcohol (10 ml) and Et$_3$N (0.5 ml) were heated under reflux for two hours. The solution was evaporated under vacuum and water (50 ml) added and organic material was extracted into ethyl acetate (2×50 ml.), washed with water, brine and dried (MgSO$_4$). The solution was evaporated under vacuum to give an oil which was dissolved in ethyl acetate and purified by flash chromatography on alumina (ICN Alumina N 32-63) using an increasing concentration of methanol in ethyl acetate (0–10%) as eluant. This gave a solid which recrystallised once from a mixture of ethyl acetate/tetrahydrofuran/isohexane and then from acetonitrile 1-(4-pyrimidinyl)-4-(1-(4-bromophenylsulphonyl)piperazin-4-ylcarbonyl)piperidine (155 mg.), as a solid, m.p. 197–198° C.;
NMR: 1.7–1.9(m, 4H), 2.6–2.8(m, 11H), 2.9–3.2(m, 6H), 3.5–3.8(bs, 4H), 4.3–4.5(dt, 2H) 6.45–6.55(dd, 1H), 7.6–7.7 (d, 2H), 7.7–7.8(d, 2H), 8.15–8.25(d, 1H), 8.6,(s, 1H); microanalysis, found: C, 48.2; H, 4.9; N, 13.9%; C$_{20}$H$_{24}$BrN$_5$O$_3$S requires: C, 48.6; H, 4.9; N, 14.2%; MS m/z 494 (MH)$^+$.

The starting material for was prepared as follows:

1-(1-(t-Butoxycarbonyl)piperidin-4-ylcarbonyloxy)2,5-dioxo pyrrolidine (2.45 g) and 1-(4-bromophenylsulphonyl)piperazine (2.31 g), were stirred together in dichloromethane (100 ml) overnight. The solution was then stirred with water (100 ml) for thirty minutes and then washed with further water, brine and dried (MgSO$_4$). The solution was evaporated under vacuum to give an oil which crystallised on standing to give 1-(1-(1-butoxycarbonyl)piperidin-4-ylcarbonyl)-4-(1-(4-bromophenylsulphonyl)piperazine (3.64 g) m.p. 209–210;
NMR: 1.45 (s, 9H), 1.49–1.81(m, 4H), 2.51(m, 1H), 2.72(dt, 2H), 3.03(t, 4H), 3.64(bs, 4H), 4.11 (d, 2H), 7.59(d, 2H), 7.69(d, 2H); MS m/z 515 (MH)$^+$.

1-(1-(t-butoxycarbonyl)piperidin-4-ylcarbonyl)-4-(1-(4-bromophenylsulphonyl)piperazine (3.3 g) was stirred in trifluoroacetic acid (20 ml) for one hour. The solvent was evaporated under vacuum and the residual oil was treated with ice and the solution basified by addition of solid K$_2$CO$_3$ Organic material was extracted into ethyl acetate and washed with water, brine and dried (MgSO$_4$) and evaporated under vacuum to give 4-(1-(4-bromophenylsulphonyl)-1-(4-piperidinylcarbonyl)piperazine as an oil (2.1 g);
NMR: 1.52–1.79(m, 4H), 2.43–2.71(m, 3H), 3.01(t, 4H), 3.13(dt, 2H), 3 .64(s, 4H), 7.61(d, 2H), 7.70(d, 2H); MS m/z 415 (MH)$^+$.

EXAMPLE 40

Using an analogous procedure to that described in Example 39; the following compounds were prepared.

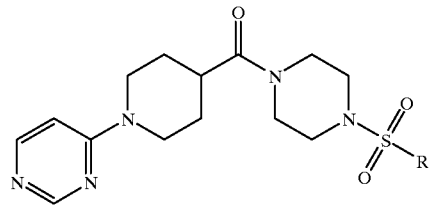

| Compound No. | Structure R = | mpt (° C.) | NMR |
|---|---|---|---|
| 1 | 4-methyl phenyl ![structure] | 186–187 | (CDCl$_3$): 1.72–1.78(m, 4H), 2.45(s, 3H), 2.65–2.76(m, 1H), 2.89–3.09(m, 6H), 3.60–3.76 (m, 4H), 4.33–4.44(m, 2H), 6.50 (dd, 1H, 6.3, 1Hz), 7.35 (d, 1H, 8.3Hz), 7.64 (d, 1H, 8.3Hz), 8.19 (d, 1H, 6.3Hz), 8.58(s, 1H). |

-continued

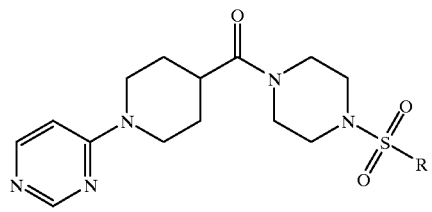

| Compound No. | Structure R = | mpt (° C.) | NMR |
|---|---|---|---|
| 2 | 4-fluoro phenyl | 189–191 | 1.71–1.78(m, 4H), 2.70–2.74 (m, 1H), 2.93–3.09(m, 6H), 3.59–3.75(m, 4H), 4.33–4.43(m, 2H), 6.49(dd, 1H, 6.3, 1Hz), 7.23–7.27 (m, 2H), 7.75–7.82(m, 2H), 8.18 (d, 1H, 6.3Hz), 8.57(s, 1H). |

EXAMPLE 41

A solution of 4-cyanobenzoyl chloride (298 mg) in methylene chloride (10 ml) was added to a stirred mixture of 1-[1(4-pyrimidinyl) piperidin-4-ylcarbonyl]piperazine (412.5 mg) and triethylamine (0.28 ml) in methylene chloride (15 ml) and the resultant mixture was stirred at ambient temperature for 2 hours. The mixture was partitioned between methylene chloride and water. The organic phase was washed with water, dried ($Na_2SO_4$) and evaporated. The residue was purified by column chromatography using 0.5% methanol in methylene chloride. Recrystallisation from ethyl acetate/hexane gave, as a solid 1-(4-cyanobenzoyl)-4-[1-(4-pyrimidinyl)piperidin-4-ylcarbonyl] piperazine (280 mg): mpt 192–193° C.;
NMR ($CDCl_3$):1.8–1.9 (m, 4H), 2.8 (m, 1H), 2.9–3.0 (m, 2H), 3.4–3.9 (m, 8H), 4.4 (d, 2H), 6.5 (d, 1H), 7.5 (d, 2H), 7.8 (d, 2H), 8.2 (dd, 1H) and 8.6 (s, 1H).

EXAMPLE 42

Using an analogous procedure to that described in Example 41: the following compounds were prepared.

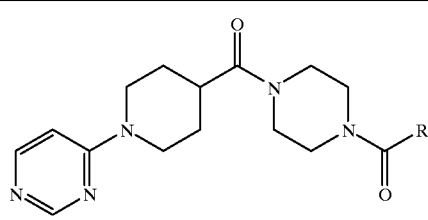

| Compound No | Structure R = | mpt (° C.) | NMR($CDCl_3$) |
|---|---|---|---|
| 1 | 4-bromophenyl | 142–145 | 1.7–1.95(m, 4H), 2.7–2.9(m, 1H), 2.9–3.1(m, 2H), 3.4–3.85(m, 8H), 4.3–4.5(m, 2H), 6.5–6.55(dd, 1H), 7.25–7.35(d, 2H), 7.55–7.65(d, 2H), 8.15–8.2(d, 1H) and 8.6(s, 1H). |

-continued

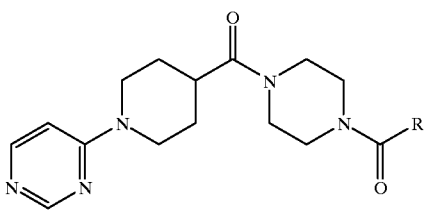

| Compound No | Structure R = | mpt (° C.) | NMR($CDCl_3$) |
|---|---|---|---|
| 2 | 4-fluorophenyl | 152–154 | 1.8–2.0(m, 4H), 2.7–2.9(m, 1H), 2.9–3.1(m, 2H), 3.4–3.9(m, 8H), 4.35–4.5(m, 2H), 6.5–6.55(d, 1H), 7.1–7.2(d, 2H), 7.4–7.5(d, 2H), 8.2–8.25(d, 1H) and 8.6(s, 1H). |
| 3 | 4-chlorophenyl | 132–135 | 1.65–1.95(m, 4H), 2.7–2.9(m, 1H), 2.95–3.1(m, 2H), 3.4–3.85(m, 8H), 4.35–4.5(m, 2H), 6.5–6.55(d, 1H), 7.32–7.48(m, 4H), 8.15–8.25(m, 1H) and 8.55–8.65(s, 1H). |

EXAMPLE 43

4-Bromobenzenesulphonyl chloride (129 mg) was added at ambient temperature to a stirred solution of 1-(4-(1-pyrimidyl)pyrrolidin-3-yl carbonyl piperazine (130 mg) in THF (8 ml) containing $Et_3N$ (0.14 ml). The mixture was stirred for 2 hours then evaporated. The residue was treated with $H_2O$ (16 ml) and $CH_2Cl_2$ (30 ml) added. Aqueous was separated and re-extracted with $CH_2Cl_2$ (20 ml). The combined organic phases were washed with saturated brine (2×10 ml), dried and evaporated. The residue was purified by chromatography on neutral alumina eluting with $CH_2Cl_2$/MeOH (99/1 v/v) to give, as a colourless solid, 1-(4-bromophenylsulphonyl)-4-(4-(1-(pyrimidyl)pyrollidin-3-ylcarbonyl)pipeazine (134 mg), mp 94–6°;
NMR ($CDCl_3$) 2.05–2.42 (m, 2H), 2.90–3.17 (m, 4H), 3.20–3.40 (m, 1H), 3.35–3.55 (m, 1H), 3.55–3.90 (m, 7H), 6.26 (dd, 1H), 7.61 (d, 2H), 7.70 (d, 2H), 8.17 (d, 1H), 8.56 (s, 1H); EI-MS m/z 480 (M+H).

The starting piperazine derivative used as starting material was prepared as follows:

Benzylchloroformate (2.86 ml) was added to a stirred suspension of N-benzyl-3-n-butoxy carbonyl pyrrolidine (1.75 g) and sodium bicarbonate (2.52 g) in $CH_2Cl_2$ (30 ml). The reaction was stirred for 0.5 hours, filtered and the filtrate evaporated to give an oil. The residual oil was purified by chromatography on silica gel; elution with EtOAc/150.$C_6H_{14}$ (1/9 v/v) gave, as a pale yellow oil, N-Cbz-3-n-butoxycarbonyl pyrrolidine (1.40 g);
NMR (CDCl$_3$) 0.93 (t, 3H), 1.27–1.47 (m, 2H), 1.52–1.67 (m, 2H), 2.06–2.22 (m, 2H), 2.95–3.10 (m, 1H), 3.33–3.75 (m, 4H), 4.07 (t, 2H), 5.12 (s, 2H), 7.25–7.40 (m, 5H), E1-MS m/z 306 (M+H).

Aqueous 1M NaOH (6 ml) was added to a stirred solution of the above ester (1.37 g) in MeOH (6 ml). After 1 hour, the methanol was evaporated. $H_2O$ (20 ml) was added to the residue and 1M HCl (6 ml) was added dropwise to the stirred mixture. This aqueous phase was extracted with EtOAc (3×25 ml). The combined organic phases were washed with saturated brine (1×20 ml) dried and evaporated to give, as a colourless oil, N-Cbz-3-carboxy pyrrolidine (780 mg);
NMR (CDCl$_3$) 2.1–2.25 (m, 2H), 3.00–3.15 (m, 1H), 3.32–3.74 (m, 4H), 5.10 (s, 2H), 7.17–7.38 (m, 5H); E1-MS m.z 248 (M-H).

N-t-Butoxycarbonyl piperazine (543 mg) was added to a solution of the above acid (727 mg) N-hydroxy benzotriazole (590 mg) in DMF (12 ml). 1-(S-Dimethylaminopropyl)-3-ethyl carbodiimide hydrochloride (612 mg) was added and the mixture stirred for 16 hours. The DMF was evaporated $H_2O$ (50 ml) was added and the aqueous phase was extracted with EtOAc (3×25 ml). The combined organic phases were washed with saturated sodium bicarbonate solution (2×20 ml). The organic phase was dried and evaporated to give, as a creamy solid, 1-t-butoxy carbonyl-4-(1-Cbz-pyrrolidin-3yl carbonyl) piperazine (1.15 g): m.p. 70–74° C.;
NMR (CDCl$_3$) 1.45 (s, 9H), 1.96–2.30 (m, 2H), 3.08–3.25 (m, 1H), 3.35–3.50 (m, 8H), 3.52–3.77 (m, 4H), 5.12 (s, 2H), 7.22–7.35 (m, 5H); E1-MS m/z 418 (M+H).

10% Pd-C (75 mg) was added to a stirred solution of the above Cbz-pyrrolidinyl derivative (1.11 g) in EtOH (40 ml) and the mixture hydrogenated at 1 atmosphere $H_2$ pressure 25° C. for 16 hours. The catalyst was removed by filtration through elite. The filtrate was evaporated to dryness to give a solid which was triturated with $Et_2O$ (10 ml) Filtration gave, as a colourless solid, 1-t-butoxycarbonyl-4-(1(H) pyrrolidin-3-yl carbonyl) piperazine (470 mg); mp 94–95° C.;
NMR (CDCl$_3$) 1.48 (s, 9H), 1.88–2.08 (m, 2H), 2.78–3.25 (m, 51H), 3.46–3.62(m, 2H); E1-MS m/z 284 (M+H).

4-Chloropyrimidine hydrochloride (210 mg) was added to a solution of the above Boc-piperazino derivative (380 mg) in EtoH (10 ml) containing Et$_3$N (0.6 ml). The mixture was stirred at reflux temperature for 16 hours. After cooling, the EtOH was evaporated. The residue was treated with saturated sodium bicarbonate solution (20 ml) and the aqueous extracted with EtOAc (3×20 ml). The combined organic phases were washed with saturated brine (2×20 ml), dried and evaporated. The residue was crystallised from ethyl acetate to give, as a pale grey solid, 1-t-butoxy carbonyl-4-(4-(1-pyrimidyl)pyrroldin-3-yl carbonyl)piperazine (301 mg); mp 156–7° C.;
NMR 1.42 (s, 9H), 1.95–2.25 (m, 2H), 3.25–3.70 (m, 13H), 6.48 (dd, 1H), 8.12 (d, 1H), 8.43 (s, 1H); E1-MS m/z 362 (M+H).

Trifluroacetic acid (ThA) (0.7 mg) was added to a stirred solution of the above pyrimidyl-pyrrolidin carbonyl piperazine derivative (261 mg) in $CH_2Cl_2$ (5 ml) at 25°. After 1 hour, TFA (0.3 ml) was added. After a further 1 hour the $CH_2Cl_2$/TFA mixture was evaporated. The residue was treated with saturated brine solution (2 ml) and 5M NaOH (2 ml). The aqueous phase was extracted with $CH_2Cl_2$ (5×15 ml). The combined organic phases were washed with saturated brine (2×25 ml), dried and evaporated to give, as a colourless solid, 1-(4-(1-pyrimidyl)pyrrolidin-3-ylcarbonyl piperazine (143 mg): m.p. 129–131° C.;

NMR (DMSOd$_6$/CD$_3$COOD) 1.95–2.25 (m, 4H), 2.97–3.20 (m, 4H), 3.30–3.85 (m, 9H), 6.45 (d, 1H), 8.09 (d, 1H), 8.45 (s, 1H); E1-MS m/z 262 (M+H).

EXAMPLE 44

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

|  | mg/tablet |
|---|---|
| (a) Tablet I |  |
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium Stearate | 1.0 |
| (b) Tablet II |  |
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |
| (c) Tablet III |  |
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |
| (d) Capsule |  |
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.
The tablet compositions (a)–(c) may be enteric coated by conventional means, for example, with cellulose acetate phthalate.

We claim:

1. A method for treating a disease or medical condition mediated at least in part by the inhibition of oxido-squaline cyclase, said method comprising administering to a warm blooded animal in need thereof an oxido-squaline cyclase inhibiting effective amount of a compound of formula I, or a pharmaceutically acceptable salt thereof $$\text{(R}^1\text{)}_m \overset{G}{\underset{N}{\diagdown}}\!\!\!-\!\!\!N\diagup\!\!\!\overset{(CH_2)_a}{\underset{(CH_2)_c}{\diagdown}}\!\!\!T^1\!\!-\!\!A\!\!-\!\!\overset{O}{\underset{\|}{C}}\!\!-\!\!T^3\!\diagup\!\!\!\overset{(CH_2)_b}{\underset{(CH_2)_d}{\diagdown}}\!\!\!T^2\!\!-\!\!XQ \qquad \text{I}$$

wherein:

G is selected from CH and N;

$T^1$ is selected from CH and N;

$R^1$ is hydrogen, amino, halogeno, cyano, (1–6C)alkyl or (1–6C)alkoxy;

m is 1 or 2;

A is selected from a direct bond and (1–4C)alkylene;

$T^2$ is selected from CH and N;

$T^3$ is selected from CH and N, provided that $T^2$ and $T^3$ are not both CH;

a and b are independently selected from 2 and 3;

c and d are independently selected from 1 and 2;

wherein the heterocyclic ring containing $T^1$ and the heterocyclic ring containing $T^2$ may, independently, be optionally substituted by one or more substituents selected from (1–6C) alkyl, (1–6C)alkoxy, phenyl(1–4C)alkyl, halogeno and (1–6C)alkoxycarbonyl;

X is selected from oxy, thio, sulphinyl, sulphonyl, carbonyl, carbonylamino, N-di-(1–6C) alkylcarbonylamino, sulphonamido, methylene, (1–4C)alkylmethylene and di-(1–6C)alkylmethylene, and when $T^2$ is CH, X may also be selected from aminosulphonyl and oxycarbonyl;

Q is selected from (5–7C)cycloalkyl, a heterocyclic moiety containing up to 4 heteroatoms selected from nitrogen, oxygen and sulphur; phenyl, naphthyl, phenyl (1–4C)alkyl and phenyl(2–6C)alkenyl, and wherein the last three groups may optionally bear a phenyl substituent; and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C) alkoxy, (3–6C)cycloalkyl, (3–6C)cycloalkyl(1–4C) alkyl, (1–4C)alkylenedioxy, (1–6C)alkylamino, di-[(1–6C)alkyl]amino, N-(1–6C)alkylcarbamoyl, di-N [(1–6C)alkyl]carbamoyl, (1–6C)alkanoylamino, (1–6C)alkoxycarbonyl, (1–6C)alkylthio, (1–6C) alkylsulphinyl, (1–6C)alkylsulphonyl, halogeno(1–6C) alkyl, (1–6C)alkanoyl, tetrazolyl and a heteroaryl group comprising a 5- or 6-membered monocyclic ring containing up to three heteroatoms selected from nitrogen, oxygen and sulphur.

2. The method as claimed in claim 1 wherein:

G is selected from CH and N; $R^1$ is hydrogen; m is 1;

$T^1$ is selected from CH and N;

A is selected from a direct bond and (1–4C)alkylene;

$T^2$ is selected from CH and N; $T^3$ is N;

wherein the heterocyclic ring containing $T^1$ and the heterocyclic ring containing $T^2/T^3$ may, independently, be optionally substituted by one or more substituents selected from (1–6C)alkyl, (1–6C)alkoxy, phenyl(1–4C)alkyl, halogeno and (1–6C)alkoxycarbonyl;

X is selected from oxy, thio, sulphinyl, sulphonyl, carbonyl and methylene;

Q is selected from phenyl, naphthyl, phenyl(1–4C)alkyl and phenyl(2–6C)alkenyl, and wherein the last three groups may optionally bear a phenyl substituent;

and wherein Q may be unsubstituted or may bear one or more substituents selected from halogeno, hydroxy, amino, nitro, cyano, carboxy, carbamoyl, (1–6C)alkyl, (2–6C) alkenyl, (2–6C)alkynyl, (1–6C)alkoxy, (3–6C)cycloalkyl, (3–6C)cycloalkyl(1–4C)alkyl, (1–4C)alkylenedioxy, (1–6C) alkylamino, di-[(1–6C)alkyl]amino, N-(1–6C) alkylcarbamoyl, di-N[(1–6C)alkyl]carbamoyl, (1–6C) alkanoylamino, (1–6C)alkoxycarbonyl, (1–6C)alkylthio, (1–6C)alkylsulphinyl, (1–6C)alkylsulphonyl, halogeno (1–6C)alkyl, (1–6C)alkanoyl and tetrazolyl.

3. The method as claimed in claim 1 or 2 wherein X is selected from $CH_2$, S, CO and $SO_2$.

4. The use as claimed in claim 3 wherein X is $SO_2$.

5. The method as claimed in claim 1 or 2 wherein $T^1$ is CH and $T^2$ and $T^3$ are both N.

6. The method as claimed in claim 1 or 2 wherein A is a direct bond.

7. The method as claimed in claim 1 or 2 wherein Q bears one or two substituents selected from halogeno, (1–6C)alkyl and (1–6C)alkoxy.

8. The method as claimed in claim 1 or 2 wherein Q comprises a phenyl moiety which bears one or more substituents independently selected from halogeno.

9. The method as claimed in claim 1 or 2 wherein Q comprises a thienyl moiety which bears one or more substituents independently selected from halogeno.

10. The method as claimed in claim 1 or 2 wherein Q comprises a naphthyl moiety which bears one or more substituents independently selected from halogeno.

11. A compound of formula I, or a pharmaceutically acceptable salt thereof $$\text{(R}^1\text{)}_m \overset{G}{\underset{N}{\diagdown}}\!\!\!-\!\!\!N\diagup\!\!\!\overset{(CH_2)_a}{\underset{(CH_2)_c}{\diagdown}}\!\!\!T^1\!\!-\!\!A\!\!-\!\!\overset{O}{\underset{\|}{C}}\!\!-\!\!T^3\!\diagup\!\!\!\overset{(CH_2)_b}{\underset{(CH_2)_d}{\diagdown}}\!\!\!T^2\!\!-\!\!XQ \qquad \text{I}$$

wherein:

G is selected from CH and N;

$T^1$ is selected from CH and N;

$R^1$ is hydrogen, amino, halogeno, cyano, (1–6C)alkyl or (1–6C)alkoxy;

m is 1 or 2;

A is selected from a direct bond and (1–4C)alkylene;

$T^2$ is N;

$T^3$ is N;

a, b, c and d are each 2;

wherein the heterocyclic ring containing $T^1$ and the heterocyclic ring containing $T^2$ may, independently, be optionally substituted by one or ore substituents selected from (1–6C) alkyl, (1–6C)alkoxy, phenyl(1–4C)alkyl, halogeno, and (1–6C)alkoxycarbonyl;

X is selected from oxy, thio, sulphinyl, sulphonyl, carbonyl, carbonylamino, N-di-(1–6C) alkylcarbonylamino, sulphonamido, methylene, (1–4C)alkymethylene and di-(1–6C)alkylmethylene, and when $T^2$ is CH, X may also be selected from aminosulphonyl and oxycarbonyl;

Q is selected from a heterocyclic moiety containing up to 4 heteroatoms selected from nitrogen, oxygen and sulphur; phenyl, naphthyl, phenyl(1–4C)alkyl and phenyl(2–6C)alkenyl, and wherein the last three groups may optionally bear a phenyl substituent; and wherein Q may be unsubstituted or may bear one or more substituents selected from halogeno, hydroxy, amino, nitro, cyano, carboxy, carbamoyl, (1–6C)alkyl, (2–6C)alkenyl, (2–6C)alkynyl, (1–6C)alkoxy, (3–6C)cycloalkyl, (3–6C)cycloalkyl(1–4C)alkyl, (1–4C)alkylenedioxy, (1–6C)alkylamino, di-[(1–6C)alkyl]amino, N-(1–6C)alkylcarbamoyl, di-N[(1–6C)alkyl]carbamoyl, (1–6C)alkanoylamino, (1–6C)alkoxycarbonyl, (1–6C)alkylthio, (1–6C)alkylsulphinyl, (1–6C)alkylsulphonyl, halogeno(1–6C)alkyl, (1–6C)alkanoyl, tetrazolyl and a heteroaryl group comprising a 5- or 6-membered monocyclic ring containing up to three heteroatoms selected from nitrogen, oxygen and sulphur.

12. The compound as claimed in claim 11 wherein A is a direct bond, the heterocyclic rings conatining $T^1$ and $T^2/T^3$ are unsubstituted, X is sulphonyl and Q is a phenyl, naphthyl, styryl or thienyl moiety and wherein Q is optionally substituted by one or more substituents selected from halogeno, (1–6C)alkyl and (1–6C)alkoxy.

13. The compound as claimed in claim 12 wherein G is N, A is a direct bond, the heterocyclic rings containing $T^1$ and $T^2/T^3$ are unsubstituted, X is sulphonyl and Q is a phenyl, naphthyl, styryl or thienyl moiety and wherein Q is optionally substituted by one or more halogeno substituents.

14. The compound as claimed in claim 11 which is selected from
1-(4-bromophenylsulphonyl)-4-(4-(1-(pyridyl)piperidin-4-ylcarbonyl)piperazine;
1-(4-bromophenylsulphonyl)-4-(4-(1-(2-methylpyrimidyl)piperidin-4-ylcarbonyl)piperazine; and
1-(4-bromophenylsulphonyl)-4-(4-(1-(pyrimidyl)piperidin-4-ylcarbonyl)piperazine; and
their pharmaceutically acceptable salts.

15. A process for preparing a compound of formula I, or a pharmaceutically acceptable salt thereof, as claimed in any one of claims 11 and 12 or 14, selected from:

(a) reacting a compound of formula II, or a reactive derivative thereof, with an amine of formula III;

(b) for the preparation of compounds of formula I in which $T^2$ is N, reacting an amine of formula IV, with a compound of formula Z—X—Q in which Z is a displaceable group;

(c) for the preparation of a compound of formula I in which $T^1$ is N, and wherein A is a direct bond, reacting a compound of formula V with an acid of formula $HO_2C$—X—Q or a reactive derivative thereof; and (d) reacting a compound of formula VI in which Z is a displaceable group with an amine of formula VII;

and whereafter, when a pharmaceutically-acceptable salt of a compound of the formula I is required, reacting said compound of formula I with the appropriate acid (which affords a physiologically acceptable anion), or with the appropriate base (which affords a physiologically acceptable cation).

16. A pharmaceutical composition comprising a compound of formula I, or a pharmaceutically-acceptable salt thereof, as claimed in any one of claims 11 to 14.

* * * * *